US012369866B2

(12) United States Patent
Brannan

(10) Patent No.: US 12,369,866 B2
(45) Date of Patent: Jul. 29, 2025

(54) ELECTROMAGNETIC NAVIGATION ASSEMBLY AND COMPUTED TOMOGRAPHY SCANNER PATIENT TABLE, SURGERY SYSTEM INCLUDING THE SAME, AND METHOD USING THE SAME

(71) Applicant: Covidien LP, Mansfield, MA (US)

(72) Inventor: Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 247 days.

(21) Appl. No.: 17/276,901

(22) PCT Filed: Dec. 3, 2019

(86) PCT No.: PCT/US2019/064115
§ 371 (c)(1),
(2) Date: Mar. 17, 2021

(87) PCT Pub. No.: WO2020/117726
PCT Pub. Date: Jun. 11, 2020

(65) Prior Publication Data
US 2021/0369215 A1 Dec. 2, 2021

Related U.S. Application Data

(60) Provisional application No. 62/775,575, filed on Dec. 5, 2018.

(51) Int. Cl.
*A61B 6/03* (2006.01)
*A61B 5/06* (2006.01)
(Continued)

(52) U.S. Cl.
CPC .............. *A61B 6/035* (2013.01); *A61B 5/062* (2013.01); *A61B 6/0407* (2013.01); *A61B 6/548* (2013.01)

(58) Field of Classification Search
None
See application file for complete search history.

(56) References Cited

U.S. PATENT DOCUMENTS 5,870,450 A * 2/1999 Khutoryansky ....... A61B 6/548
378/197
2004/0199072 A1 10/2004 Sprouse et al.
(Continued)

FOREIGN PATENT DOCUMENTS

CN 106821498 A 6/2017
DE 102008032313 B3 12/2009

OTHER PUBLICATIONS

International Search Report and Written Opinion of the International Searching Authority issued in corresponding International Appl. No. PCT/US2019/064115 mailed Feb. 14, 2020 (14 pages).
(Continued)

*Primary Examiner* — Katherine L Fernandez
(74) *Attorney, Agent, or Firm* — Carter, DeLuca & Farrell LLP

(57) ABSTRACT

An EM device is provided that includes an antenna assembly for radiating at least one electromagnetic field for electromagnetic navigation. The EM device also includes a moving arrangement coupled to the antenna assembly and configured to either move the antenna assembly toward and away from a CT scan plane or move a patient toward and away from the antenna assembly. An operating system is provided that includes a CT scanner defining a CT scan plane, and a patient table housing an antenna assembly and a moving arrangement. A method is provided that includes engaging a moving arrangement to move a patient, activating the CT scanner, and activating the antenna of an electromagnetic navigation system.

7 Claims, 16 Drawing Sheets

(51) Int. Cl.
*A61B 6/00* (2006.01)
*A61B 6/04* (2006.01)

(56) References Cited

U.S. PATENT DOCUMENTS

| | | | |
|---|---|---|---|
| 2006/0025668 A1 | 2/2006 | Peterson et al. | |
| 2007/0003010 A1* | 1/2007 | Guertin | A61B 6/4441 |
| | | | 378/63 |
| 2010/0008475 A1* | 1/2010 | Maschke | A61B 5/06 |
| | | | 5/601 |
| 2010/0299014 A1* | 11/2010 | Bouvier | A61B 6/4405 |
| | | | 701/25 |
| 2012/0122062 A1* | 5/2012 | Yang | G09B 19/003 |
| | | | 434/219 |
| 2014/0275998 A1 | 9/2014 | Eichler et al. | |
| 2014/0350387 A1* | 11/2014 | Siewerdsen | A61B 6/4441 |
| | | | 600/436 |
| 2018/0123248 A1* | 5/2018 | Morgan | H04B 5/00 |
| 2021/0113164 A1* | 4/2021 | Wong | A61N 5/1049 |

OTHER PUBLICATIONS

Chinese Office Action issued in corresponding application CN 201980080810.3 dated Aug. 30, 2023 (8 pages) (English translation not available).
European Examination Report issued in corresponding application EP 19828022.4 dated Dec. 1, 2023 (7 pages).

* cited by examiner

ELECTROMAGNETIC NAVIGATION ASSEMBLY AND COMPUTED TOMOGRAPHY SCANNER PATIENT TABLE, SURGERY SYSTEM INCLUDING THE SAME, AND METHOD USING THE SAME

CROSS-REFERENCE TO RELATED APPLICATIONS

This application is a U.S. National Stage Application filed under 35 U.S.C. § 371 (a) of International Patent Application Serial No. PCT/US2019/064115, filed Dec. 3, 2019, which claims the benefit of the filing date of provisional U.S. Patent Application No. 62/775,575 filed Dec. 5, 2018.

BACKGROUND

Technical Field

The present disclosure relates to patient tables with electromagnetic navigation (EMN) systems for use with computed tomography (CT) scanners, systems using such patient tables, and methods for using such patient tables. More particularly, the present disclosure relates to a patient table that enables alternating use of EMN systems and CT scanners to avoid interference with the CT scanner by the EMN system.

Discussion of Related Art

Electromagnetic (EM) navigation (EMN) has helped expand medical imaging, diagnosis, prognosis, and treatment capabilities by enabling a location and/or an orientation of a medical device to be accurately determined while the device is within the body of a patient. One example of a medical procedure in which EMN is employed is ELECTROMAGNETIC NAVIGATION BRONCHOSCOPY® (ENB™), which includes a planning phase and a navigation phase. During the planning phase, a computed tomography (CT) scan of the chest of the patient is used to generate a virtual three-dimensional bronchial map of the patient and a planned pathway for the navigation phase. During the navigation phase, an antenna assembly radiates an electromagnetic field throughout the chest of the patient, a practitioner inserts into the airway of the patient an electromagnetic sensor that senses the radiated electromagnetic field, and a computing device determines a location and/or an orientation (e.g., relative to the planned pathway) of the electromagnetic sensor based on characteristics of the sensed electromagnetic field.

To enable accurate determination of sensor location and/or orientation, a detailed mapping of electromagnetic field measurements at respective sensor locations is generated. Generating such a mapping, however, requires taking precise electromagnetic field measurements at many (for example, hundreds of thousands or more) locations within the expected electromagnetic volume, which is a laborious and time-consuming process that, in some cases, requires expensive machines.

The burden of generating electromagnetic field mappings increases in circumstances where multiple antenna assemblies are employed. For example, in order to enable an electromagnetic sensor to reach deeper portions of the body of the patient, and/or remain within the body during subsequent medical procedures without interfering with additional medical devices, it may be desirable to employ a small electromagnetic sensor, such as a single-coil electromagnetic sensor. However, to employ a small electromagnetic sensor for EMN while maintaining the ability to determine multiple (for example, six) degrees of freedom of the sensor, multiple antenna assemblies may be required to increase the number of radiated electromagnetic fields to be sensed. In such a case, the above-noted exhaustive mapping procedure may need to be conducted for each antenna assembly design. Moreover, given potential variations from manufacturing, the mapping procedure may even need to be completed for each instance of a specific antenna assembly design (i.e., each individual antenna assembly manufactured).

Given the foregoing, a need exists for improved electromagnetic navigation antenna assemblies and methods for designing such antenna assemblies.

An ablation system may be used with an electromagnetic ultrasound guided needle tracking. The ablation system may be used for intraoperative procedures where ultrasound imaging is used without real time CT imaging. The EM field generator is placed under the patient anatomy targeted for intervention. This configuration is not compatible to real time CT based interventions due to the location of the field generator existing within the CT imaging plane. A large portion of the ablation procedures take place within the interventional CT suite. Therefore, there is a need for an EMN system to be used within an interventional CT suite.

SUMMARY

According to an aspect of the present disclosure, an EM device is provided that includes an antenna assembly for radiating at least one electromagnetic field for electromagnetic navigation. The EM device also includes a moving arrangement coupled to the antenna assembly and configured to either move the antenna assembly toward and away from a CT scan plane or move a patient toward and away from the antenna assembly.

In another aspect of the present disclosure, the moving arrangement moves the antenna assembly in a direction perpendicular to the CT scan plane.

In a further aspect of the present disclosure, the moving arrangement moves the antenna assembly in a foot-to-head trajectory of a patient table.

In yet another aspect of the present disclosure, the EM device may also include a user interface operable to control movement of the moving arrangement. The user interface may be a hand held remote control, a cable tethered switch, or a button on a graphical user interface electrically coupled to a processor.

In another aspect of the present disclosure, the moving arrangement includes a rail structure and/or a plurality of wheels. The moving arrangement may be operable by manual operation, an electric motor, and/or an electromagnet.

In a further aspect of the present disclosure, the EM device may also include a patient table housing the antenna assembly and the moving arrangement.

In yet another aspect of the present disclosure, a portion of the patient table that remains within the CT scan plane when the moving arrangement moves the antenna assembly away from the CT scan plane includes CT compatible materials.

In another aspect of the present disclosure, the patient table may be configured to move between a first position and a second position. The patient in the first position may be located above the antenna assembly to enable tracking of surgical tools, and the patient in the second position may be located in the CT scan plane.

In a further aspect of the present disclosure, an operating system is provided that includes a CT scanner defining a CT scan plane, and a patient table housing an antenna assembly and a moving arrangement. The antenna assembly may radiate at least one electromagnetic field for electromagnetic navigation. The moving arrangement may be configured to move the antenna assembly away from and toward the CT scan plane and the patient toward and away from the CT scan plane. The moving arrangement may be adapted to enable a patient to cross the CT scan plane.

In yet another aspect of the present disclosure, a method is provided that includes engaging a moving arrangement to move a patient into a scan plane of a CT scanner or move an antenna of an electromagnetic navigation system away from the scan plane of the CT scanner. The method also includes activating the CT scanner to obtain a CT scan of the patient. The method further includes engaging the moving arrangement to move the patient away from the scan plane of the CT scanner or move the antenna of the electromagnetic navigation system toward the scan plane of the CT scanner. The method also includes activating the antenna of the electromagnetic navigation system.

Any of the above aspects and embodiments of the present disclosure may be combined without departing from the scope of the present disclosure.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which.

DETAILED DESCRIPTION

Figure 1:
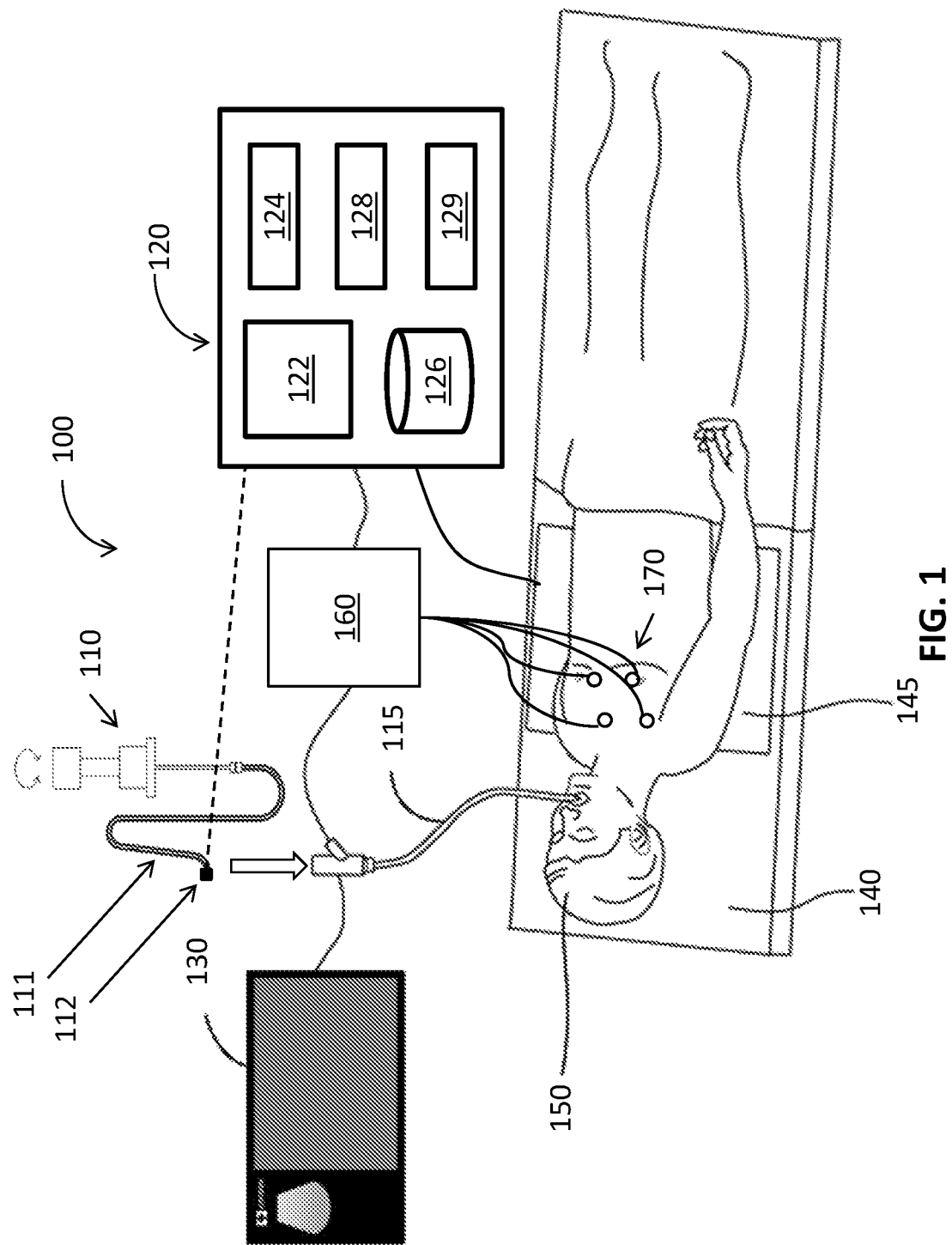
FIG. 1 is a perspective view of an example electromagnetic navigation (EMN) system in accordance with an embodiment of the present disclosure.

Electromagnetic (EM) field generators are commonly used as a component in surgical tool tracking systems for medical applications. CT imaging may also be used within medical procedures involving EM tracking. The field generator can be placed underneath the patient such that the tracking field is deployed within the patient. The field generator creates significant CT imaging distortion. Therefore the EM field generator should not be within the CT imaging plane while CT imaging takes place. The present technology discloses a mechanism that enables movement of the field generator out of the CT imaging plane prior to CT imaging taking place. Alternatively, the present technology enables movement of a patient from an area of the EM field generator to the CT imaging plane, and back again. A user interface is disclosed as well as an integration approach to existing EM tracking systems.

An EM field generator that is housed within a structure of rails and/or beams enables movement of the EM field generator along a horizontal plane common to the food-to-head trajectory of a CT gantry table (also referred to as a patient table and/or a CT table). Alternatively, the present technology provides for a moving system to move the patient back and forth between the CT gantry and the EM field generator. The structure is composed of CT compatible materials for the portion which would be within the CT scanning plane. The materials that are not within the CT scanning plane do not need to be CT compatible. The EM field generator may reside within a wheeled cart (alternatively the EM field generator may have wheels mounted to it directly and therefore not need a separate cart) which rolls within the structure between at least two positions. In position A, the field generator is located beneath the patient anatomy targeted for CT imaging and surgical interventions, specifically the interventional tactics involving EM tracked surgical tools. In position B, the field generator is located behind (away from CT gantry side of table) the patient anatomy targeted for CT imaging and surgical interventions.

The user may select the location of the EM field generator by either manually pushing and/or pulling the generator between positions with a rod, rope, and/or handle coupled to the generator, activating an electric motor which engages a mechanism to move the field generator (by, for example, a worm drive, pulley, or cable, etc.), or activating an electromagnet to pull the generator into the position not favored by gravity (likely the CT imaging position). The user interface may be a hand held remote control or cable tethered button and/or switch to select the position. Alternatively, the accessory may directly connect to the ablation platform CPU through a simple communication interface (for example, a cable or wireless link). The field generator position control may be a button on a GUI.

Using an EMN system compatible with an interventional CT suite saves significant development time and investment. The present technology enables a user friendly and high performing EM tracked ultrasound guided needle placement within procedures using real time CT imaging.

The present disclosure is directed to antenna assemblies for radiating electromagnetic fields for electromagnetic navigation, electromagnetic navigation systems that include such antenna assemblies, and computer-implemented methods of designing such antenna assemblies. In one example, by virtue of geometrical and other aspects of an antenna assembly herein, the need to generate and employ a detailed electromagnetic field mapping can be avoided by instead enabling an electromagnetic field mapping, theoretically computed based on characteristics of the antenna assembly, to be employed either alone or in conjunction with a more easily generated low-density electromagnetic field mapping obtained from measurements. In other words, the antenna assembly herein can serve as the basis upon which to generate an accurate high-density theoretical electromagnetic field mapping for EMN, without having to use expensive measuring equipment and without having to perform time-consuming and laborious measurements.

In another example, an antenna assembly herein includes on a single substrate multiple planar antennas having characteristics, such as geometries and/or relative locations that are diverse from one another, that enable multiple (for example, six) degrees of freedom of a small electromagnetic sensor, such as a single-coil sensor, to be determined.

In yet another example, an antenna assembly herein includes a trace that is deposited on a layer of a substrate and that forms multiple loops with the spacing between loops and the spacing from a boundary or edge of the substrate that result in efficient use of the available area of the substrate.

In a further example, an automated, or semi-automated, highly reproducible computer-implemented method for designing an antenna assembly is provided herein. An antenna assembly design generated in this manner can be exported into a printed circuit board (PCB) layout software tool to minimize the need for a large amount of manual layout. The antenna assembly design can also be exported into an electromagnetic field simulator software tool to enable the generation of a theoretical electromagnetic field mapping for the antenna assembly.

Detailed embodiments of antenna assemblies, systems incorporating such antenna assemblies, and methods of designing the same are described herein. These detailed embodiments, however, are merely examples of the disclosure, which may be embodied in various forms. Therefore, specific structural and functional details disclosed herein are not to be interpreted as limiting, but merely as a basis for the claims and as a representative basis for enabling one skilled in the art to variously employ the present disclosure in virtually any appropriately detailed structure. While the example embodiments described below are directed to the bronchoscopy of a patient's airways, those skilled in the art will recognize that the same or similar assemblies, systems, and methods may also be used in other lumen networks, such as, for example, the vascular, lymphatic, and/or gastrointestinal networks.

FIG. 1 illustrates an example electromagnetic navigation (EMN) system 100 provided in accordance with the present disclosure. In general, the EMN system 100 is configured to identify a location and/or an orientation of a medical device being navigated toward a target location within the patient's body by using, among other things, an antenna assembly that generates one or more electromagnetic fields that are sensed by a sensor affixed to the medical device. In some cases, the EMN system 100 is further configured to augment computed tomography (CT) images, magnetic resonance imaging (MRI) images, and/or fluoroscopic images employed during navigation of the medical device through the patient's body toward a target of interest, such as a deceased portion in a luminal network of the patient's lung.

The EMN system 100 includes a catheter guide assembly 110, a bronchoscope 115, a computing device 120, a monitoring device 130, a patient platform 140 (which may be referred to as an EM board), a tracking device 160, and reference sensors 170. The bronchoscope 115 is operatively coupled to the computing device 120 (by way of the tracking device 160) and the monitoring device 130 via respective wired connections (as shown in FIG. 1) or wireless connections (not shown in FIG. 1).

During a navigation phase of an EMN bronchoscopy procedure, the bronchoscope 115 is inserted into the oral cavity of a patient 150 and captures images of the luminal network of the lung. The catheter guide assembly 110 is inserted into the bronchoscope 115 to access the periphery of the luminal network of the lung of the patient 150. The catheter guide assembly 110 may include a catheter or extended working channel (EWC) 111 with an EM sensor 112 affixed to a portion (for example, a distal portion) of the EWC 111. A locatable guide catheter (LG) may be inserted into the EWC 111 with another EM sensor (not shown in FIG. 1) affixed to a portion (for example, a distal portion) of the LG. The EM sensor 112 affixed to the EWC 111 or the EM sensor affixed to the LG is configured to receive a signal based on an electromagnetic field radiated by the antenna assembly 145, and based upon the received signal, is used to determine a location and/or an orientation of the EWC 111 or the LG during navigation through the luminal network of the lung. Due to the size restriction of the EM sensor 112 relative to the EWC 111 or the LG, in some cases the EM sensor 112 may include only a single coil for receiving one or more EM signals generated by way of an antenna assembly 145 as described in further detail below. However, the number of coils in the EM sensor 112 is not limited to one but may be two, three, or more.

The computing device 120, such as a laptop, desktop, tablet, or other suitable computing device, includes a display 122, one or more processors 124, one or more memories 126, an AC current driver 127 for providing AC current signals to the antenna assembly 145, a network interface controller 128, and one or more input devices 129. The particular configuration of the computing device 120 illustrated in FIG. 1 is provided as an example, but other configurations of the components shown in FIG. 1 as being included in the computing device 120 are also contemplated. In particular, in some embodiments, one or more of the components (122, 124, 126, 127, 128, and/or 129) shown in FIG. 1 as being included in the computing device 120 may instead be separate from the computing device 120 and may be coupled to the computing device 120 and/or to any other component(s) of the system 100 by way of one or more respective wired or wireless path(s) to facilitate the transmission of power and/or data signals throughout the system 100. For example, although not shown in FIG. 1, the AC current driver 127 may, in some example aspects, be separate from the computing device 120 and may be coupled to the antenna assembly 145 and/or coupled to one or more components of the computing device 120, such as the processor 124 and the memory 126, by way of one or more corresponding paths.

In some aspects, the EMN system 100 may also include multiple computing devices 120, wherein the multiple computing devices 120 are employed for planning, treatment, visualization, or helping clinicians in a manner suitable for medical operations. The display 122 may be touch-sensitive and/or voice-activated, enabling the display 122 to serve as both an input device and an output device. The display 122 may display two-dimensional (2D) images or three-dimensional (3D) images, such as a 3D model of a lung, to enable a practitioner to locate and identify a portion of the lung that displays symptoms of lung diseases.

The one or more memories 126 store one or more programs and/or computer-executable instructions that, when executed by the one or more processors 124, cause the one or more processors 124 to perform various functions and/or procedures. For example, the processors 124 may calculate a location and/or an orientation of the EM sensor 112 based on the electromagnetic signal that is radiated by the antenna assembly 145 and received by the EM sensor 112. The processors 124 may also perform image-processing functions to cause the 3D model of the lung to be displayed on the display 122. The processors 124 may also generate one or more electromagnetic signals to be radiated by way of the antenna assembly 145. In some embodiments, the computing device 120 may further include a separate graphic accelerator (not shown in FIG. 1) that performs only the image-processing functions so that the one or more processors 124 may be available for other programs. The one or more memories 126 also store data, such as mapping data for EMN, image data, patients' medical record data, prescription data, and/or data regarding a history of the patient's diseases, and/or other types of data.

The mapping data may link multiple grid points, in a coordinate system of an EM volume in which a medical device (e.g., the EWC 111, the LG, treatment probe, or another surgical device) navigates, to the EM signal characteristics (for example, signal strength) that correspond to the grid points, respectively. In this manner, when the EM sensor 112 senses an EM signal having certain characteristics at a particular grid point, the one or more processors 124 may compare the sensed EM signal characteristics to the EM signal characteristics in the mapping data and determine the location and/or orientation of the EM sensor 112 within the EM volume based on a result of the comparison.

As shown in FIG. 1, the platform 140 is configured to provide a flat surface upon which the patient 150 lies during the EMN navigation procedure. The antenna assembly 145, which may also be referred to as an EM field generating device, is arranged upon the platform 140 or is included as a component of the platform 140. The antenna assembly 145 includes one or more antennas, such as planar loop antennas (not shown in FIG. 1). Example aspects of the antenna assembly 145 are described in further detail below.

With the patient 150 lying upon the platform 140, the one or more processors 124 (or another signal generator not shown in FIG. 1) generate and provide to the antenna(s) of the antenna assembly 145 by way of the AC current driver 127 one or more AC current signals that the antenna(s) convert into one or more respective EM signal(s) and radiate in a manner sufficient to surround a portion of the patient 150. In some aspects, the antenna assembly 145 includes a connector that has at least two terminals, and the trace of the antenna (not shown in FIG. 1) has two ends that are coupled to the two connector terminals, respectively, to form a signal communication path from the one or more processors 145 to the antenna.

Figure 2:
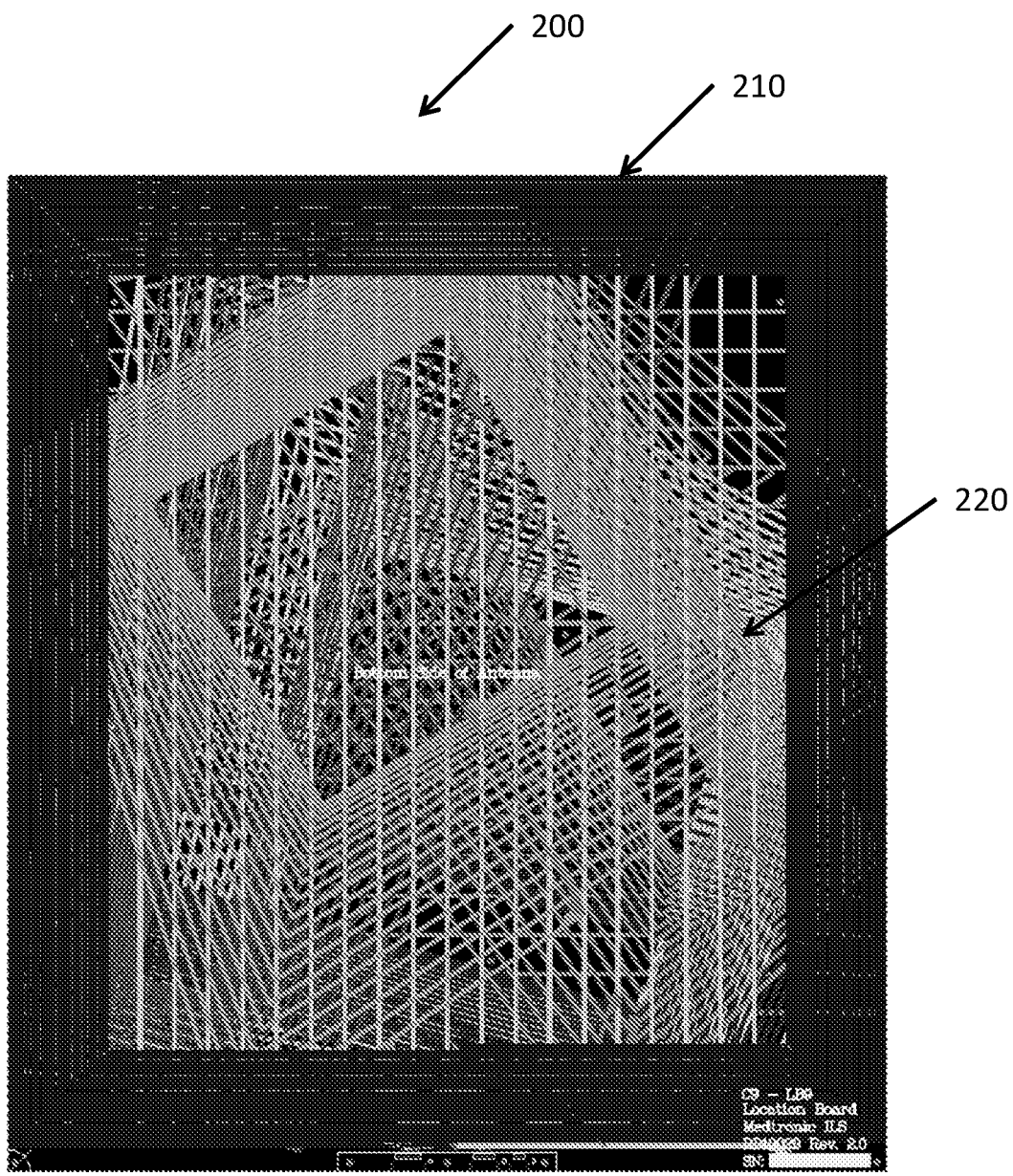
FIG. 2 shows an example design of an antenna assembly of the EMN system in accordance with an embodiment of the present disclosure.

Having described an example EMN system 100, reference will now be made to FIG. 2, which is a graphical illustration of an example antenna assembly layout 200 of the antenna assembly 145 of the EMN system 100, according to an embodiment of the present disclosure. The antenna assembly layout 200 includes a substrate 210, such as a printed circuit board (PCB), which is formed of an electrically insulating material and may include one or more layers. The antenna assembly layout 200 also includes multiple planar antennas 220, which are formed of an electrically conductive material, such as a PCB trace, deposited on the substrate 210 and arranged in multiple loops or as a coil. In one example, each of the planar antennas 220 is deposited on a respective one of the layers of the substrate 210. In the example antenna assembly layout 200 of FIG. 2, multiple layers of the substrate 210 are shown simultaneously.

Each of the multiple antennas may be configured to radiate a separate EM field, for example, using frequency division multiplexing and/or time division multiplexing controlled by the processors 124 or by another generator. For example, the antennas, in some aspects, may be configured to radiate multiple EM fields sufficient in number and/or sufficient in diversity of characteristics (such as frequency, time, modulation scheme, and/or the like) to enable a single-coil electromagnetic sensor mounted on the EWC 111, or on any other medical device, to be used to determine the location and/or the orientation of the sensor, the EWC 111, and/or the medical device. The antenna assembly 145 may, for instance, include six to nine or more loop antennas. In some embodiments, for each of the loop antennas, the distances between its adjacent loops increase as the loops become larger. For example, for each of the planar antennas, respective distances between adjacent pairs of loops may increase in a direction from an innermost one of the loops to an outermost one of the loops of the respective planar antenna. In various embodiments, two or more of the loop antennas of the antenna assembly 145 may have a same number of loops, or may have respectively different numbers of loops.

Having described an example antenna assembly layout 200 of an antenna assembly 145 of the EMN system 100, reference will now be made to FIG. 3, which is a flowchart illustrating an example procedure 300 for designing an antenna assembly such as the antenna assembly 145, in accordance with an embodiment of the present disclosure. In various embodiments, the procedure 300 may be fully computer-implemented or partially computer-implemented. Reference will also be made to FIGS. 4 through 13, which are graphical illustrations of certain steps of the procedure 300, in accordance with an embodiment of the present disclosure. The example method 300 of FIG. 3 may be implemented to design an antenna assembly that includes one antenna or an antenna assembly that includes multiple antennas. For illustrative purposes, the present description of the method 300 will be made in the context of designing an antenna assembly that includes multiple antennas. However, although certain aspects of the method 300 will be described only with respect to the design of a single one of the multiple antennas, those aspects of the method 300 apply similarly to the other ones of the multiple antennas.

Before describing the details of the procedure 300, an overview of the procedure 300 will be provided. In general, according to the procedure 300, the design of the antenna assembly is based on a set of design parameters and/or constraints including a number of antennas M of the antenna assembly to be designed, as well as, for each antenna of the antenna assembly, a seed shape for the antenna, a location of a centroid of the seed shape on the substrate upon which the antenna will be manufactured, a number of loops (N) of the antenna, a minimum trace center-to-center spacing (TCCM) for the antenna, and dimensions of an edge or a boundary of the substrate. Locations of antenna vertices of the antenna are determined based on the seed shape. The antenna design then proceeds by interconnecting the antenna vertices by way of straight linear portions, beginning with the innermost antenna vertices and progressing to the outermost antenna vertices, so that the entire antenna forms a coil including a single trace arranged in multiple loops. In an aspect, each loop of the antenna assembly grows from the seed shape toward the boundaries of the substrate and effectively covers most of the available surface area of the substrate layer outside of the seed shape. The two ends of the trace are routed to a connector location to enable the antenna to be coupled to a signal generator.

For antenna assemblies having multiple planar antennas on respective layers of the multiple layer substrate, this general procedure is repeated for each of the antennas. Additionally, data corresponding to the designed antenna layouts can be exported to an electromagnetic field simulation tool for simulating the electromagnetic field (for example, the theoretical electromagnetic field mapping for EMN described above) that the respective antennas would generate based on their particular characteristics. The data corresponding to the designed antenna layouts can also be exported to a PCB manufacturing tool to enable the antenna assembly to be manufactured in an automated manner, in accordance with the designed antenna layouts.

Figure 4:
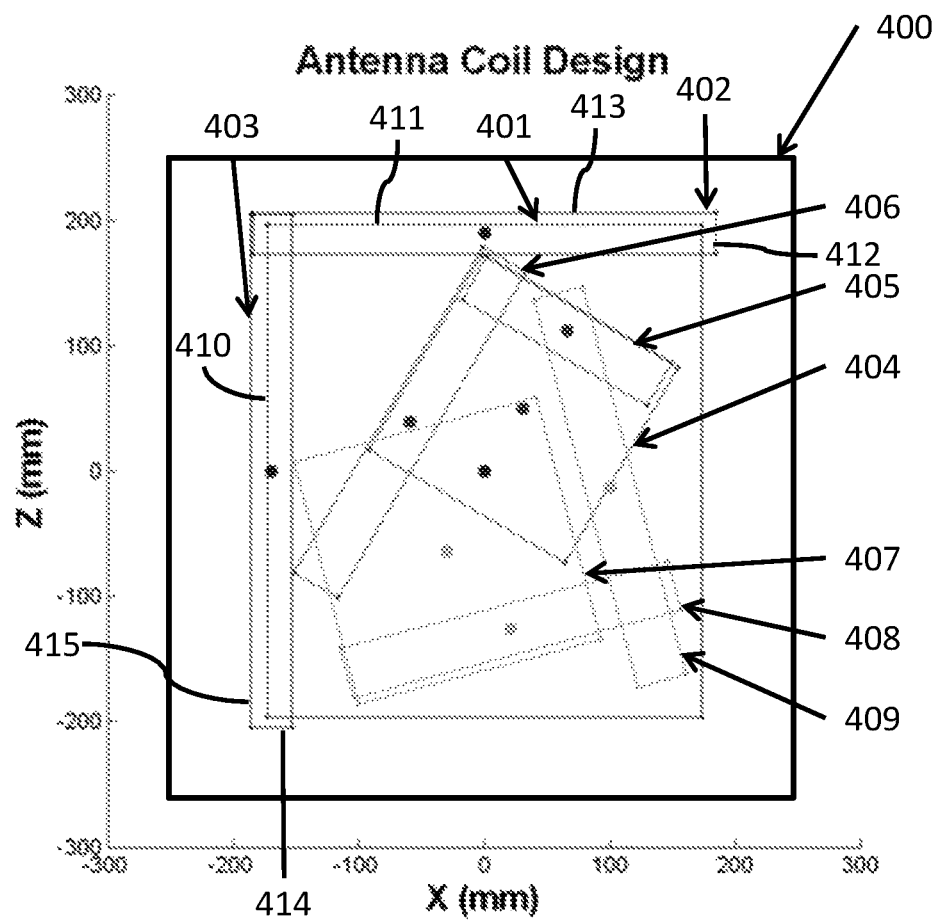
FIGS. 4-11 are example graphical representations of certain aspects of the procedure of FIG. 3, in accordance with an embodiment of the present disclosure.

Before describing the details of the procedure 300, reference will be made to FIG. 4 to describe example seed shapes and their characteristics. In particular, FIG. 4 shows examples of nine seed rectangles 401 through 409 of an antenna assembly to be designed according to the procedure 300. Each of the seed rectangles 401 through 409 includes four vertices within the edge 400 of the substrate. The number of seed rectangles, and hence the number of antennas M, shown in the example of FIG. 4 is nine, however, this is for illustrative purposes only and should not be construed as limiting. In other embodiments, the number of seed shapes, and hence the number of antennas M, may be, for example, six, nine, or more. As an example, the square 400 may represent the edge of the substrate, and a boundary (not shown in FIG. 4) that represents the area of the substrate that is available for placement of the antennas may be formed from a square within the x-z plane that is contained within the edge 400 of the substrate and smaller than the edge 400 of the substrate by some predetermined threshold or buffer amount.

In another example, an antenna assembly herein includes on a single substrate (for example, on respective layers of a multiple-layer substrate) multiple planar antennas having characteristics, such as geometries and/or relative locations that are diverse from one another, that enable multiple (for example, six) degrees of freedom of a small electromagnetic sensor, such as a single-coil sensor, to be determined. For instance, as shown in FIG. 4, the nine seed rectangles 401-409 may be grouped in three, with seed rectangles 401-403 being in a first group; seed rectangles 404-406 being in a second group; and seed rectangles 407-409 being in a third group. As shown in FIG. 4, the three seed rectangles in each group have specific geographical relationships with respect to one another. For instance, one seed rectangle is a square (or substantially square-like), and the other two seed rectangles are non-square rectangles and are located near two sides of the square. For example, the seed rectangle 401 is a square, the seed rectangle 402 is located in line with the length of the seed rectangle 401, and the seed rectangle 403 is located in line with the width of the seed rectangle 401. Further, the length of the seed rectangle 402 is longer than the width of the square 401, and is similar to the length of the seed rectangle 401, while the width of the seed rectangle 402 is smaller than the width of the square 401; and the width of the seed rectangle 403 is longer than the length of the square 401 and is similar to the width of the square 401, while the length of the seed rectangle 402 is smaller than the length of the square 401. The seed rectangles 404-406 of the second group and the seed rectangles 407-409 of the third groups also have the similar geometric features as the seed rectangles 401-403 of the first group.

Put differently, for each of multiple groups of planar antennas that may be generated based on the seed rectangles 401-409: an innermost loop of the first planar antenna (for example, corresponding to the seed rectangle 401) has a first linear portion (for example, first linear portion 410) and a second linear portion (for example, second linear portion 411) approximately perpendicular to the first linear portion (for example, first linear portion 410); an innermost loop of the second planar antenna (for example, corresponding to the seed rectangle 402) has a first linear portion (for example, first linear portion 412) and a second linear portion (for example, second linear portion 413) approximately perpendicular to, and longer than, the first linear portion (for example, first linear portion 412); an innermost loop of the third planar antenna (for example, corresponding to the seed rectangle 403) has a first linear portion (for example, first linear portion 414) and a second linear portion (for example, second linear portion 415) approximately perpendicular to, and longer than, the first linear portion (for example first linear portion 414); the first linear portion (for example, first linear portion 412) of the seed rectangle of the innermost loop of the second planar antenna is approximately parallel to the first linear portion (for example, first linear portion 410) of the innermost loop of the first planar antenna; and the first linear portion (for example, first linear portion 414) of the innermost loop of the third planar antenna is approximately parallel to the second linear portion (for example, second linear portion 411) of the innermost loop of the first planar antenna. Although additional reference numbers for the first and second linear portions of the seed rectangles 404-409 (and hence the correspondence planar antennas) are omitted from FIG. 4 for clarity, the seed rectangles 404-406 of the second group and the seed rectangles 407-409 of the third groups each have similar geometric relationships with respect to one another, as those described above in the context of the seed rectangles 401-403 of the first group.

In an aspect, these three groups may be geometrically dispersed from each group within the substrate 210. Dispersion may be accomplished by geometric relationship and/or angular relationship. For example, the respective innermost loops of the planar antennas of each group can be positioned, on the respective layers of the multiple-layer substrate, at respective angles that are distinct from one another. Additionally, the planar antennas, and/or the seed rectangles upon which the planar antennas are based, may have respective centroids (for example represented by circular dots in FIG. 4), relative to a plane of the substrate, that are mutually distinct from one another. Further, the outer boundaries of the first group include all seed rectangles 404-409 of the second and third groups. Also, the seed rectangles 404-409 of the second and third groups are geometrically dispersed within the outer boundaries of the first group.

Further, each group has an angular relationship with respect to the two axes (i.e., the x axis and the z axis). For example, the seed rectangle 401 of the first group is congruent with the two axes, while the seed rectangles 404 and 407 of the second and third groups are angled with respect to the two axes with different angles, respectively. In other words, the smallest angle between the seed rectangle 401 or the square of the first group and the x axis is zero; the smallest angle between the seed rectangle 404 and the x axis is greater than zero but less than the smallest angle between the seed rectangle 407 of the third group and the x axis. However, the relationship among three groups is not limited to the geometric and angular relationships but can be expanded in any readily conceivable way for a person having ordinary skill in the art within the scope of this disclosure.

Four vertices of each of the seed rectangles 401-409 may be provided in a coordinate form (x, z) in the x-z plane. In an aspect, a centroid of each of the seed rectangles 401-409 may also be provided in coordinate form or can be calculated from the four vertices. Dispersion may also be achieved by dispersing the centroids within the substrate 210. In an aspect, centroids of all seed rectangles 401-409 are disposed on the substrate in positions that are distinct from each other.

Figure 3:
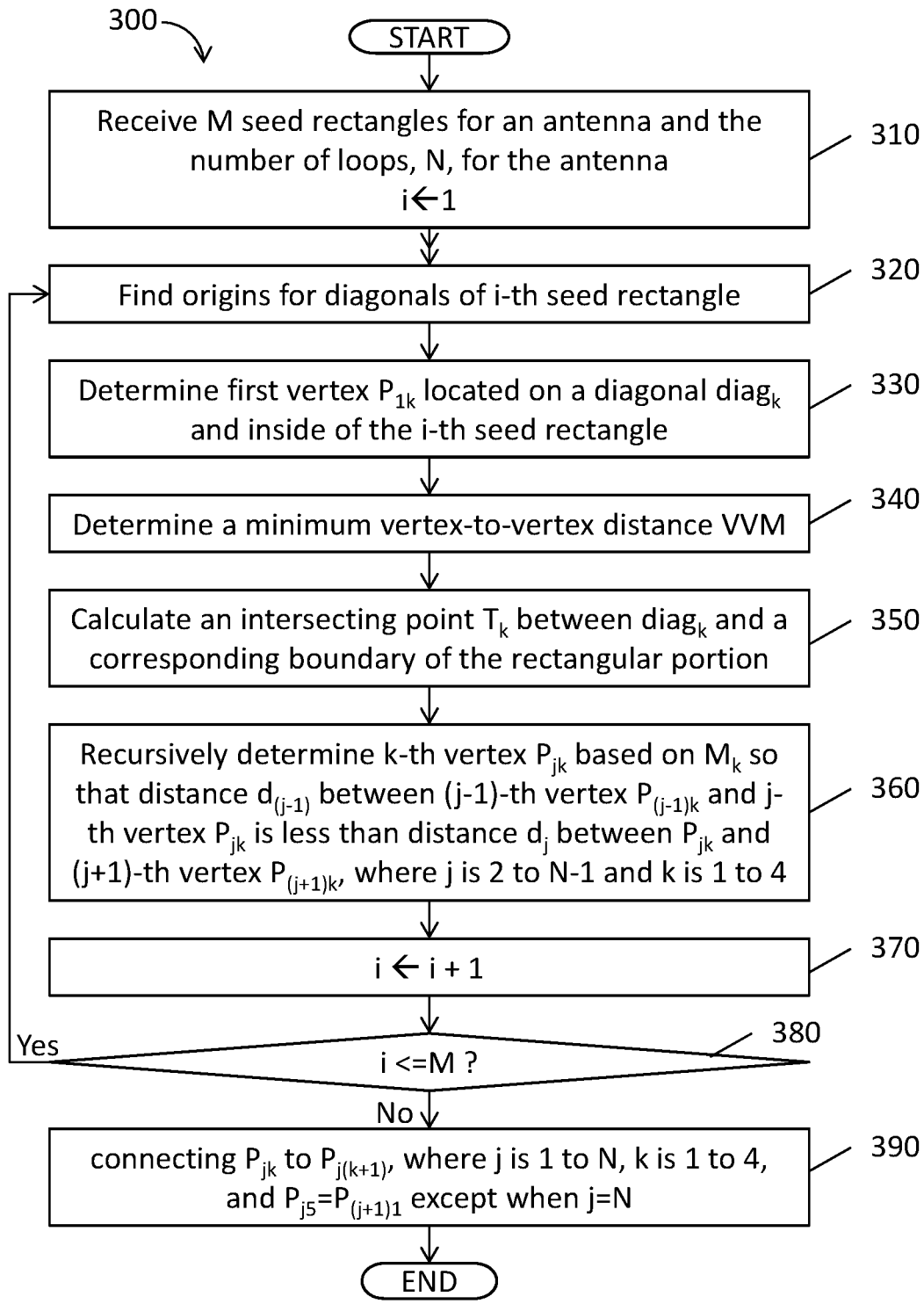
FIG. 3 is a flowchart illustrating an example procedure for designing an antenna assembly in accordance with an embodiment of the present disclosure.

Referring now to FIG. 3, prior to block 301, a set of design parameters and/or constraints for the first antenna of the antenna assembly to be designed (for example, a seed shape for the antenna, a location of a centroid of the seed shape on a substrate upon which the antenna will be manufactured, a number of loops (N) of the antenna, a minimum trace center-to-center spacing (TCCM) for the antenna, and dimensions of an edge or a boundary of the substrate) are set (not shown in FIG. 3). For illustrative purposes, the seed shapes utilized in the procedure 300 for each antenna are seed rectangles; however, this should not be construed as limiting. Other seed shapes (for example, a seed triangle, a seed pentagon, a seed hexagon, any convex polygon, convex curved shape (e.g., an ellipse, an egg, a circle, etc.), or any other suitable seed shape) are contemplated and can be employed in the procedure 300. In some embodiments, any combination of different seed shapes can be used for the antennas of the antenna assembly, respectively. Each seed shape has multiple vertices. More specifically, each seed rectangle has four vertices.

At block 301, an antenna index $i_{antenna}$ is initialized. For example, $i_{antenna}$ is set equal to 1 to correspond to the first antenna of the multiple (M, where M>1) antennas of the antenna assembly to be designed. As described below, the purpose of the antenna index $i_{antenna}$ is to enable the procedure 300 to be repeated, in the case of antenna assemblies including multiple antennas, for each antenna of the M antennas of the antenna assembly. For instance, in some examples, the substrate has multiple layers (for example, as in a multi-layer PCB) and the method 300 is employed to generate multiple planar antenna layouts corresponding to the antennas to be deposited on corresponding ones of the multiple layers of the substrate.

At block 302, multiple diagonal lines are computed, relative to a coordinate system of the substrate, based on the seed rectangle. In general, the number of diagonal lines computed at block 302 equals the number of vertices of the seed shape. In particular, in the case of the seed rectangle, which has four vertices, four diagonal lines are computed that bisect the four vertices of the seed rectangle, respectively, and extend from the four vertices of the seed rectangle, respectively, to the boundary of the substrate. The boundary of the substrate may be a physical boundary of the substrate, such as an edge of a PCB, or may be a theoretically imposed boundary, such as a boundary offset from the edge of the PCB by a predetermined buffer distance.

Figure 5:
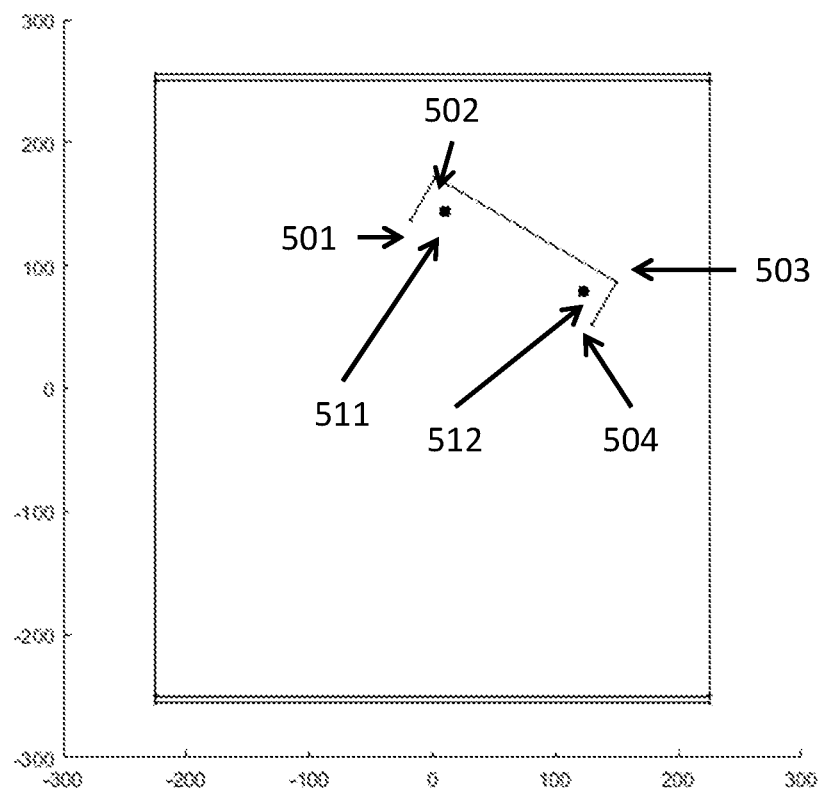

In one example, as part of the computing of the multiple diagonal lines performed at block 302, origins for the diagonal lines of each of vertex of the seed rectangle are first calculated, and then vertices of the innermost loop of the antenna (also referred to as seed vertices) are determined based on the seed rectangle. For example, FIG. 5 shows origins 511 and 512 that are calculated for the seed rectangle 405 of FIG. 4. The origins 511 and 512 are bounded by the four vertices 501 through 504 of the seed rectangle 405. In an aspect, one origin may correspond to a single vertex of the seed rectangle, or one origin may correspond to two adjacent vertices. In another aspect, the origins 511 and 512 may be located on the diagonals of the seed rectangle or on the diagonals which bisect the corresponding angle to form two 45 degree angles. In this case, diagonals define the locations of vertices of the loop antenna. As an example, the origin 511 is located on a diagonal, which bisects the 90 degree angle at the vertex 501 to form two 45 degree angles. Also as shown in FIG. 5, the origin 511 is located on the intersection of the diagonals which bisect the angles at vertices 501 and 502. In the same way, the origin 512 is located at the intersection of the diagonals which bisect the angles at vertices 503 and 504. In one example, the origins for the diagonal lines of each vertex of the seed rectangle can be calculated by performing principal component analysis (PCA) over the coordinates of the four vertices 501-504, utilizing singular value decomposition. The following notations are used herein:

$P_{jk}$ represents the k-th vertex of the j-th loop, where j is 1 to N and k is 1 to 4;

$P_{jkx}$ and $P_{jkz}$ represent x-coordinate and z-coordinate of the vertex $P_{jk}$, respectively;

$\{P_{j1}, P_{j2}, P_{j3}, P_{j4}\}$ or simply $\{P_{jk}\}$ is a 4 by 2 matrix having four vertices $P_{j1}, P_{j2}, P_{j3}, P_{j4}$ of the j-th loop as its rows;

U represents a 4 by 4 matrix having orthonormal eigenvectors of $\{P_{jk}\}\{P_{jk}\}^T$ as its column;

V represents a 2 by 2 matrix having orthonormal eigenvectors of $\{P_{jk}\}^T\{P_{jk}\}$ as its column; and S represents a 4 by 2 matrix, whose nonzero elements are located only at its diagonal and are square root of eigenvalues of $\{P_{jk}\}\{P_{jk}\}^T$ or $\{P_{jk}\}^T\{P_{jk}\}$; and $\tilde{S}$ represents a 4 by 2 matrix, whose nonzero elements are located only at its diagonal and are equal to the smallest nonzero element of S.

Given the four vertices $R_k$, $(R_{kx}, R_{kz})$, of the i-th seed rectangle, a centroid C, $(C_x, C_z)$, of the i-th seed rectangle is calculated as follows:

$$(C_x, C_z) = \left(\frac{\sum_{k=1}^{4} R_{kx}}{4}, \frac{\sum_{k=1}^{4} R_{kz}}{4}\right). \quad (1)$$

By performing singular value decomposition on the centroid-subtracted four vertices $R_j$, S, V, and D matrices are obtained as follows:

$$USV^T = \{R_k - C\} \quad (2),$$

where $\{R_k - C\}$ is a 4 by 2 matrix, each row of $\{R_k - C\}$ is the centroid-subtracted vertex $(R_{kx} - C_x, R_{kz} - C_z)$, and k is 1 to 4.

S is a 4 by 2 matrix having nonzero elements only in the diagonal, i.e., $S_{11}$ and $S_{22}$. Based on the singular value decomposition, $S_{11}$ is greater than or equal to $S_{22}$. By replacing the value of $S_{11}$ with the value of $S_{22}$, we can get a new 4 by 2 diagonal matrix $\tilde{S}$, where $\tilde{S}_{11}$ and $\tilde{S}_{22}$, are equal to $S_{22}$. Then, the origins $O_k$ for each vertex can be obtained by the following:

$$\{O_k\} = \{R_k\} - U\tilde{S}V^T \quad (3).$$

Because the diagonal entries of $\tilde{S}$ are the minimum values of the diagonal entries of S, $\{O_k\}$ includes only two different rows, corresponding to the origins 511 and 512, within the i-th seed rectangle, as shown in FIG. 5.

After obtaining the origins 511 and 512, a first set of four seed vertices $P_{1k}$ within the i-th seed rectangle are determined. These first four seed vertices $P_{1k}$ are the seed vertices for the innermost loop of the respective antenna and can be used to determine the other vertices of that antenna.

Figure 6:
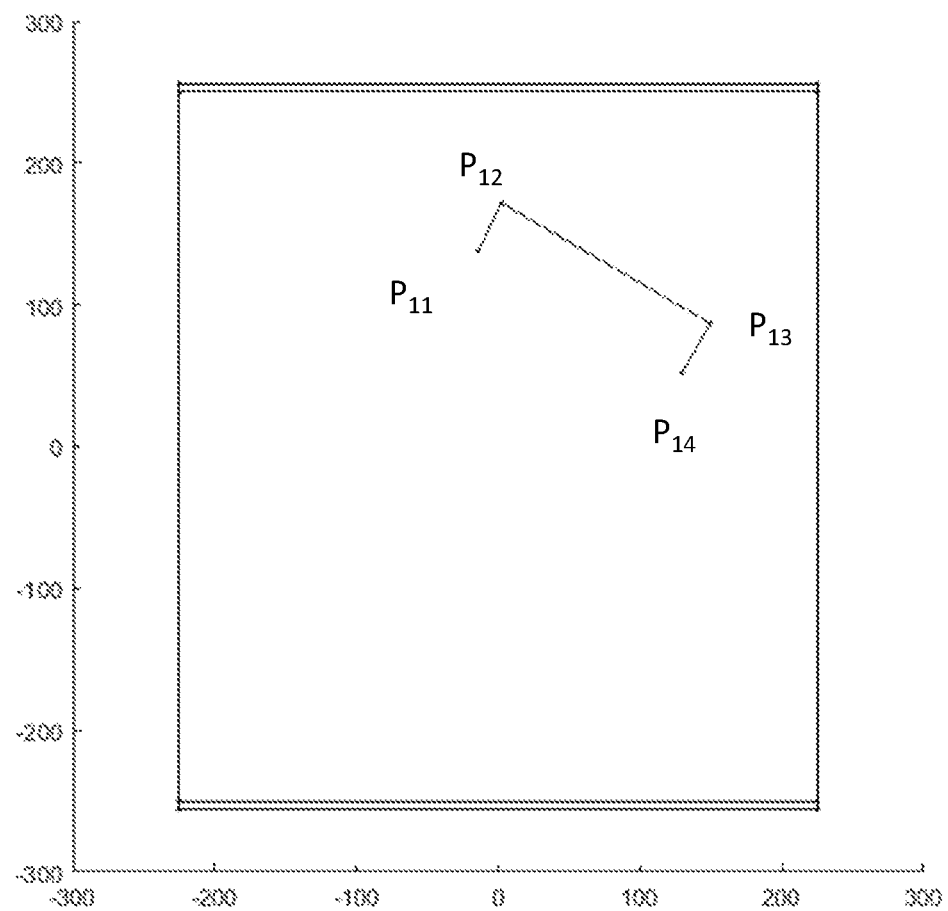
Figure 7:
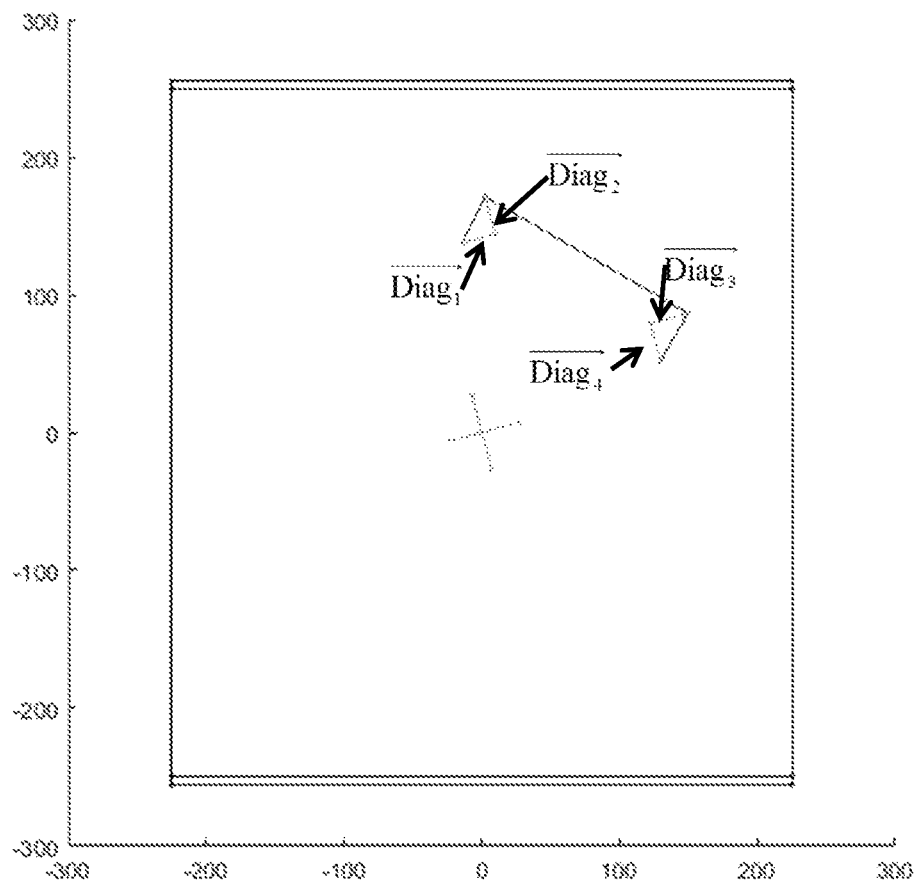

Given the minimum trace center-to-center (TCCM) spacing, which represents a predetermined minimum distance between traces or loops of a particular antenna or of all the antennas of a particular antenna assembly, the first seed vertex $P_{11}$ is determined by moving $R_1$ into its corresponding diagonal, which bisects the 90 degree angle at $R_1$, toward the inside of the i-th seed rectangle. This can be done by first defining two vectors from $R_1$ as follows:

$$\vec{V}_{R_{14}} = \vec{R}_4 - \vec{R}_1 \tag{4}$$

$$\vec{V}_{R_{12}} = \vec{R}_2 - \vec{R}_1 \tag{5}$$

where $\vec{R}_k$ is a vector pointing toward $R_k$ from the respective origin $O_k$, $\vec{V}_{R_{14}}$ is a vector pointing toward $R_4$ from $R_1$, and $\vec{V}_{R_{12}}$ is a vector pointing toward $R_2$ from $R_1$. By adding the unit vector of $\vec{V}_{R_{14}}$, $$\frac{\vec{V}_{R_{14}}}{\|\vec{V}_{R_{14}}\|},$$

to the unit vector of $\vec{V}_{R_{12}}$, $$\frac{\vec{V}_{R_{12}}}{\|\vec{V}_{R_{12}}\|},$$

a vector having a direction in line with the respective diagonal line, which bisects the 90 degree angle at $R_1$ to form two 45 degree angles, is obtained, where the symbol "$\|$ $\|$" represents a magnitude of the vector inside of the symbol "$\|$ $\|$". Then, the first seed vertex $P_{11}$ is obtained by the following equation:

$$\vec{P}_{11} = \vec{R}_1 + TCCM \times \left( \frac{\vec{V}_{R_{14}}}{\|\vec{V}_{R_{14}}\|} + \frac{\vec{V}_{R_{12}}}{\|\vec{V}_{R_{12}}\|} \right), \tag{6}$$

where $\vec{P}_{11}$ is a vector originating from the respective origin $O_1$ and thus represents a coordinate of $P_{11}$. FIG. 6 illustrates the other three seed vertices $P_{12}$, $P_{13}$, and $P_{14}$ of the antenna, which match $R_2$, $R_3$, and $R_4$. The smallest distance between $P_{1k}$ and the four sides of the i-th seed rectangle equals TCCM. FIG. 7 shows vectors $Diag_1$, $Diag_2$, $Diag_3$, and $Diag_4$, which may form respective portions of the diagonal lines that bisect the seed vertices $P_{11}$, $P_{12}$, $P_{13}$, and $P_{14}$ and extend from the respective seed vertices $P_{11}$, $P_{12}$, $P_{13}$, and $P_{14}$ to the boundary of the substrate.

Referring back to FIG. 3, at block 303 a diagonal line index $i_{diagonal}$ is initialized. For example, $i_{diagonal}$ is set equal to 1 to correspond to the first diagonal line of the four diagonal lines of the seed rectangle. As described below, the purpose of the diagonal line index $i_{diagonal}$ is to enable aspects of the procedure to be repeated for each of the diagonal lines of the seed rectangle.

At block 304, for the respective diagonal line, a vertex-layout-distance (also referred to herein as a layout distance) $V_{layout\_k}$ between the respective vertex of the seed rectangle and the boundary of the substrate, along the respective diagonal line is computed. The layout distance may represent, or may be related to, the maximum usable distance between the respective vertex of the seed rectangle and the boundary of the substrate.

Figure 9:
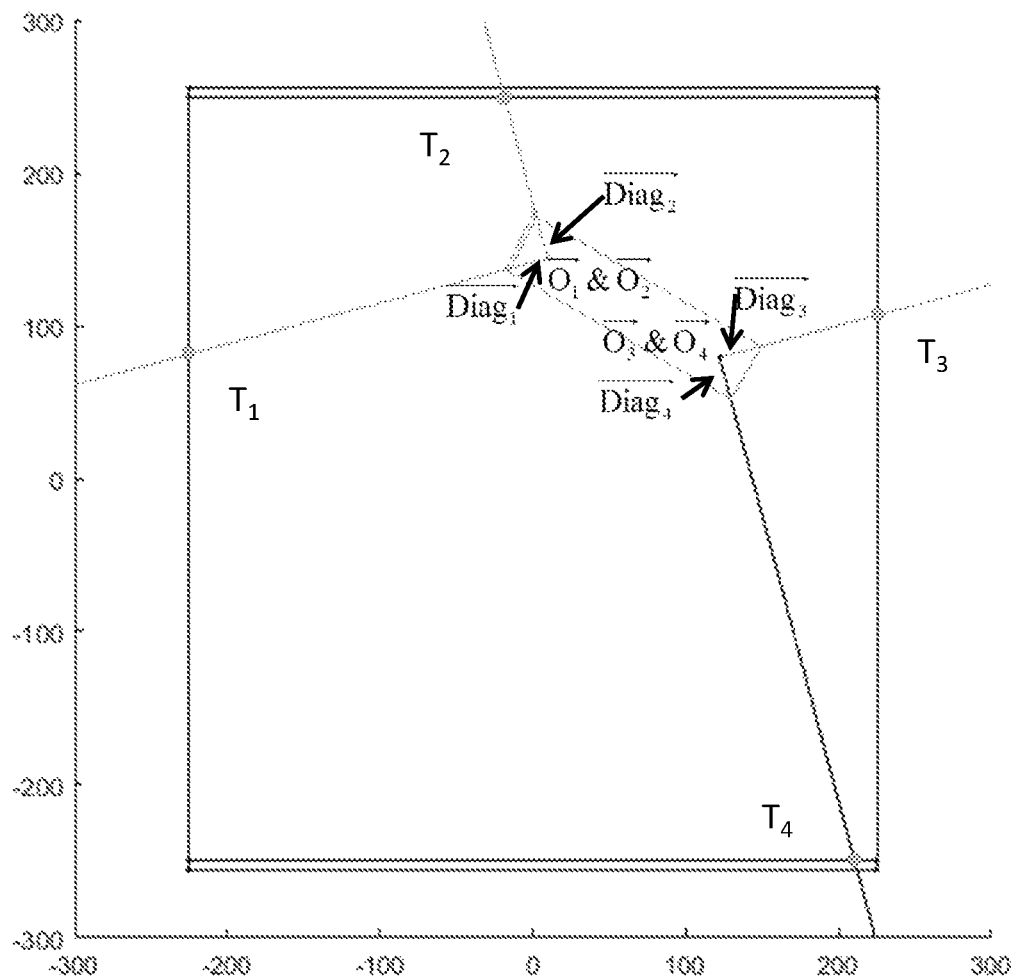

In some example embodiments, as part of the computing of the layout distance at block 304, respective intersecting points $T_k$ between the origins $O_k$ and the boundary of the substrate, when the respective diagonals $\vec{Diag}_k$ are projected from the origins $O_k$, are calculated and identified, as shown, for example, in FIG. 9. The intersecting points $T_k$ can be found using multiple conventional approaches. When the intersecting points $T_k$ are found, the following relationship is satisfied:

$$\frac{\vec{O_k T_k}}{\|\vec{O_k T_k}\|} = \frac{\vec{Diag_k}}{\|\vec{Diag_k}\|}, \tag{14}$$

where $\vec{O_k T_k}$ is a vector from the origin $O_k$ to the intersecting point $T_k$. In other words, vector $\vec{O_k T_k}$ has the same direction as the diagonal vector $\vec{Diag_k}$.

With the four vertices $P_{11}$, $P_{12}$, $P_{13}$, and $P_{14}$ of the first loop and the intersecting points $T_1$, $T_2$, $T_3$, and $T_4$ identified, the vertex-layout-distance, $V_{layout\_k}$, can be calculated from the following equation:

$$V_{layout\_k} = \|\vec{P_{1k} T_k}\| - \frac{VVM}{2}. \tag{15}$$

The subtracting term, $$\frac{VVM}{2},$$

ensures that the last vertex $P_{Nk}$ of the N-th loop is distant from the intersecting point $T_k$. In other words, only a $V_{layout\_k}$-long linear portion starting from $P_{1k}$ is used to distribute (N−1) vertices between $P_{1k}$ and $T_k$.

After the intersecting points $T_k$ are identified, every vertex for the loop antenna can be determined. As one of the initial conditions is that the number of loops of the loop antenna is N and the four vertices $P_{11}$, $P_{12}$, $P_{13}$, and $P_{14}$ of the first loop are determined in step 330, four vertices of each of the second, third, . . . , and N-th loops are recursively determined. In particular, at block 305, for the respective diagonal line, respective distances between adjacent pairs of planar antenna vertices to be positioned along the respective diagonal line are determined based at least in part on the layout distance computed at block 304. For example, the respective distances between adjacent pairs of planar antenna vertices to be positioned along the respective diagonal line may be determined so as to fit the predetermined number of loops N of the antenna while maximizing the use of the available linear distance from the vertex of the seed rectangle to the boundary of the substrate. In this manner, the available area of the substrate may be efficiently utilized. Additionally, in some example aspects, an outermost planar antenna vertex of the planar antenna vertices of the respective planar antenna is distanced from the boundary of the substrate by not more than a predetermined threshold, for efficient utilization of the available substrate area.

Figure 10:
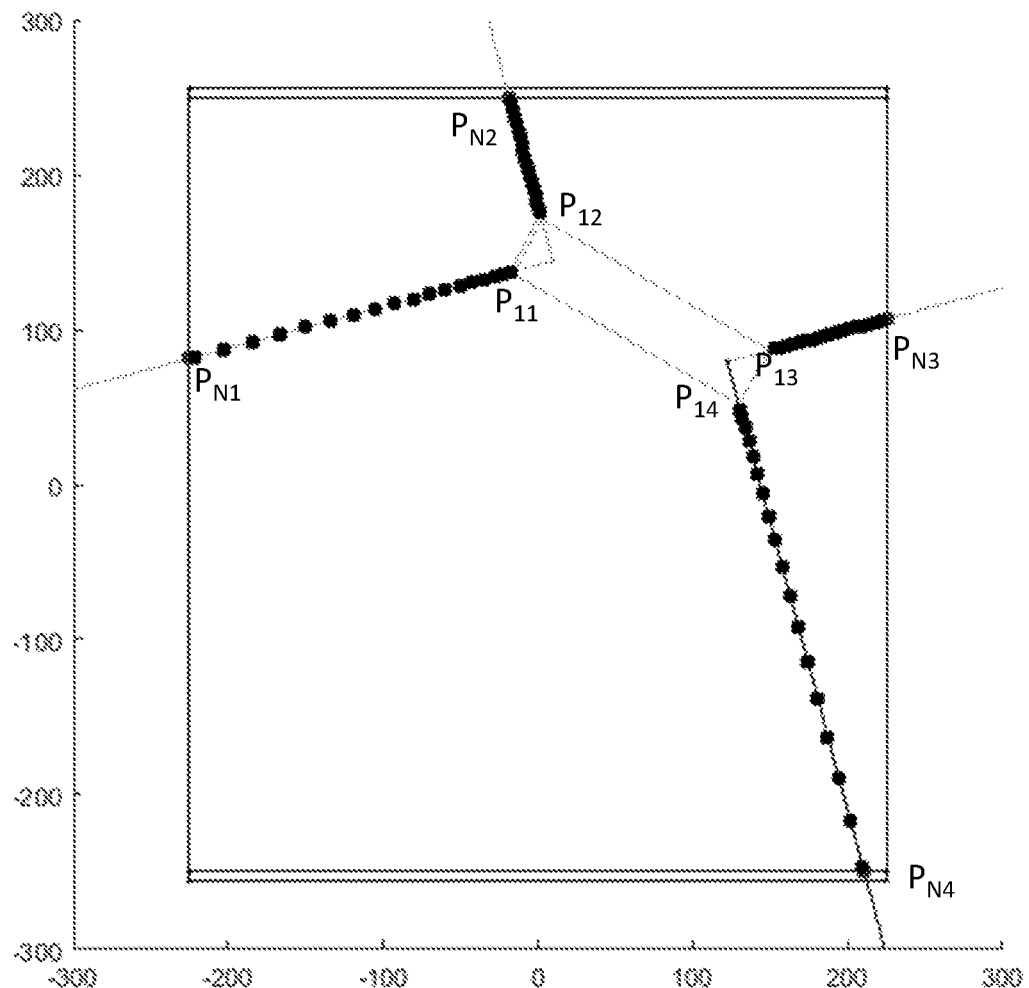

In some examples, the respective distances are determined at block 305 based at least in part on the predetermined number N of loops of the planar antenna, a predetermined minimum spacing between adjacent vertices, a predetermined minimum spacing between adjacent traces, and/or any combination of one or more of those factors or other factors. In particular, in one example, vertices are grouped in four groups with each group forming a rectangular shape, and vertices in the same group are described as corresponding vertices. For example, the first group includes $P_{11}$, $P_{21}$, . . . , and $P_{N1}$, the second group includes $P_{12}$, $P_{22}$, . . . , and $P_{N2}$, the third group includes $P_{13}$, $P_{23}$, . . . , and $P_{N3}$, and the fourth group includes $P_{14}$, $P_{24}$, . . . , and $P_{N4}$. Thus, $P_{3k}$ and $P_{Nk}$ are in the same k-th group and are corresponding vertices, while $P_{33}$ and $P_{42}$ are not in the same group and cannot be corresponding vertices. For each group, the distance between $P_{jk}$ and $P_{(j+1)k}$ is set to be greater than the distance between $P_{(j-1)k}$ and $P_{jk}$, where j is 2 to N−1 and k is 1 to 4. In other words, the distance between two adjacent corresponding vertices is increasing toward the boundary of the substrate. Put differently, in one example, as illustrated in FIG. 10, the distances between the adjacent pairs of antenna vertices become progressively larger in a direction from an innermost one of the vertices to an outermost one of the vertices. The progressively increasing distance in a direction from the respective vertex of the seed rectangle to the boundary may be implemented by various methods, such as arithmetic progression, geometric progression, exponential progression, and/or the like.

For example, arithmetic progression may be employed to distribute remaining vertices in each group. Letting $d_{jk}$ be the distance between $P_{jk}$ and $P_{(j+1)k}$ in the k-th group and be expressed in recursive form as:

$$\|\overrightarrow{P_{jk}P_{(j+1)k}}\| = d_{jk} \qquad (16),$$

$$d_{jk} = slope_k \times (j-1) + d_{1k} \qquad (17), \text{ and}$$

$$d_{1k} = VVM \qquad (18),$$

where $\|\overrightarrow{P_{jk}P_{(j+1)k}}\|$ represents a distance between vertices $P_{jk}$ and $P_{(j+1)k}$, $slope_k$ is a constant for the k-th group, which is the common difference between two distances $d_{jk}$ and $d_{(j+1)k}$, and j is 1 to (N−2). Thus, each vertex in the k-th group is positioned on the linear portion connecting $T_k$ and $P_{1k}$ and the total length between $P_{Nk}$ and $P_{1k}$ is less than or equal to the vertex-layout-distance, $V_{layout\_k}$. In order to make an additional keepout area of half the minimum trace center to center (TCCM) spacing between the $T_k$ and $P_{Nk}$, the following equation may be satisfied:

$$\sum_{j=1}^{N-1} \|\overrightarrow{P_{jk}P_{(j+1)k}}\| = V_{layout\_k} - \frac{TCCM}{2}, \qquad (19)$$

or $$\sum_{j=1}^{N-1} d_{jk} = \sum_{j=1}^{N-1} (slope_k \times (j-1) + d_{lk}) = V_{layout\_k} - \frac{TCCM}{2}. \qquad (20)$$

When equation (20) is solved for the constant, $slope_k$, the following equation can be obtained:

$$slope_k = \frac{2 \cdot \left(V_{layout\_k} - (N-1)d_{lk} - \frac{TCCM}{2}\right)}{(N-1)(N-2)}. \qquad (21)$$

When the equation (20) is combined with equations (16) and (17), the following equation is obtained:

$$\|\overrightarrow{P_{jk}P_{(j+1)k}}\| = \frac{2 \cdot \left(V_{layout\_k} - (N-1)d_{lk} - \frac{TCCM}{2}\right)}{(N-1)(N-2)}(j-1) + d_{lk}. \qquad (22)$$

In this way, the distance between two adjacent corresponding vertices $P_{jk}$ and $P_{(j+1)k}$ increases as j increases. This progressive pattern between corresponding vertices is shown in FIG. 10 more clearly in the first and the fourth groups than in the second and the third groups.

At block 306, the planar antenna vertices are positioned along the respective diagonal line based on the respective distances between adjacent pairs of planar antenna vertices determined at block 305.

At block 307, the diagonal line index $i_{diagonal}$ is compared to the number of diagonal lines, namely four, of the seed rectangle to determine whether the procedures of block 305 and block 306 are to be repeated for additional diagonal lines of the respective antenna. If it is determined at block 307 that $i_{diagonal}$ is less than the number of diagonal lines, then at block 308 $i_{diagonal}$ is incremented by one to correspond to the next diagonal line (for example, the second diagonal line) of the four diagonal lines of the seed rectangle. Then the procedures of block 305 and block 306 are repeated for that next diagonal line in the manner described above.

If, on the other hand, it is determined at block 307 that $i_{diagonal}$ is equal to the number of diagonal lines, indicating that the procedures of block 305 and block 306 have been executed for each of the four diagonal lines of the seed rectangle, then at block 309, a minimum vertex to vertex distance (VVM) is calculated to make sure that, when vertices are connected by linear portions or segments of a line, the smallest distance between two adjacent corresponding linear portions is greater than TCCM, where the phrase "two adjacent corresponding linear portions" being used to refer to linear portions that are positioned in different loops but are located closer to one another than any other linear portions. This is done by defining diagonal vectors $\overrightarrow{Diag_k}$, setting up temporary vertices P'$_{21}$ and P'$_{22}$, measuring a distance between a linear portion connecting the temporary vertices P'$_{21}$ and P'$_{22}$ and a linear portion connecting $P_{11}$ and $P_{12}$, and adjusting a value of VVM until the smallest distance is greater than TCCM. Details of this step are further described below.

The diagonal vectors $\overrightarrow{Diag_k}$ are defined as follows:

$$\overrightarrow{Diag_k} = \overrightarrow{P_{1k}} - \overrightarrow{O_k} \qquad (7),$$

where k is 1 to 4. When these diagonal vectors $\overrightarrow{Diag_k}$ are arranged at the origin (0, 0), they form a cross indicating that they form four 90 degree angles as shown in the middle of FIG. 7.

A temporary distance $D_{p2to5}$ is initialized as the value of TCCM. Vectors $\overrightarrow{V_{P_{32}}}$, $\overrightarrow{P'_{22temp}}$, and $\overrightarrow{V_{P_{22temp}}}$ are defined by the following:

$$\overrightarrow{V_{P_{32}}} = \overrightarrow{P_{12}} - \overrightarrow{P_{13}}, \qquad (8)$$

$$\overrightarrow{P'_{22temp}} = \overrightarrow{P_{12}} + D_{p2to5} \times \frac{\overrightarrow{V_{P_{32}}}}{\|\overrightarrow{V_{P_{32}}}\|}, \qquad (9)$$

and

-continued $$\vec{V_{P_{22}temp}} = \vec{P'_{22temp}} - \vec{P_{12}}. \quad (10)$$

Temporary vertex P'$_{22}$ is defined in a vector form as follows:

$$\vec{P'_{22}} = \vec{P_{12}} + \frac{\vec{Diag_2}}{\|\vec{Diag_2}\|} \times \frac{\|\vec{V_{P_{22}temp}}\|^2}{\vec{V_{P_{22}temp}} \cdot \frac{\vec{Diag_2}}{\|\vec{Diag_2}\|}}, \quad (11)$$

where the symbol "·" is a dot product between two vectors. In short, temporary vertex P'$_{22}$ is distant from P$_{12}$ by $\sqrt{2}\times$TCCM in a direction of the diagonal $\vec{Diag_2}$ toward outside of the i-th seed rectangle. Next, VVM is temporarily initialized with the following equation:

$$VVM = \|\vec{P'_{22}} - \vec{P_{12}}\| \quad (12).$$

Temporary vertex P'$_{21}$ is defined in a vector form as follows:

$$\vec{P'_{21}} = \vec{P_{11}} + VVM \times \frac{\vec{Diag_1}}{\|\vec{Diag_1}\|}. \quad (13)$$

As with P'$_{22}$, temporary vertex P'$_{21}$ is distant from P$_{11}$ by $\sqrt{2}\times$TCCM in a direction of the diagonal $\vec{Diag_1}$ toward outside of the i-th seed rectangle.

Figure 8:
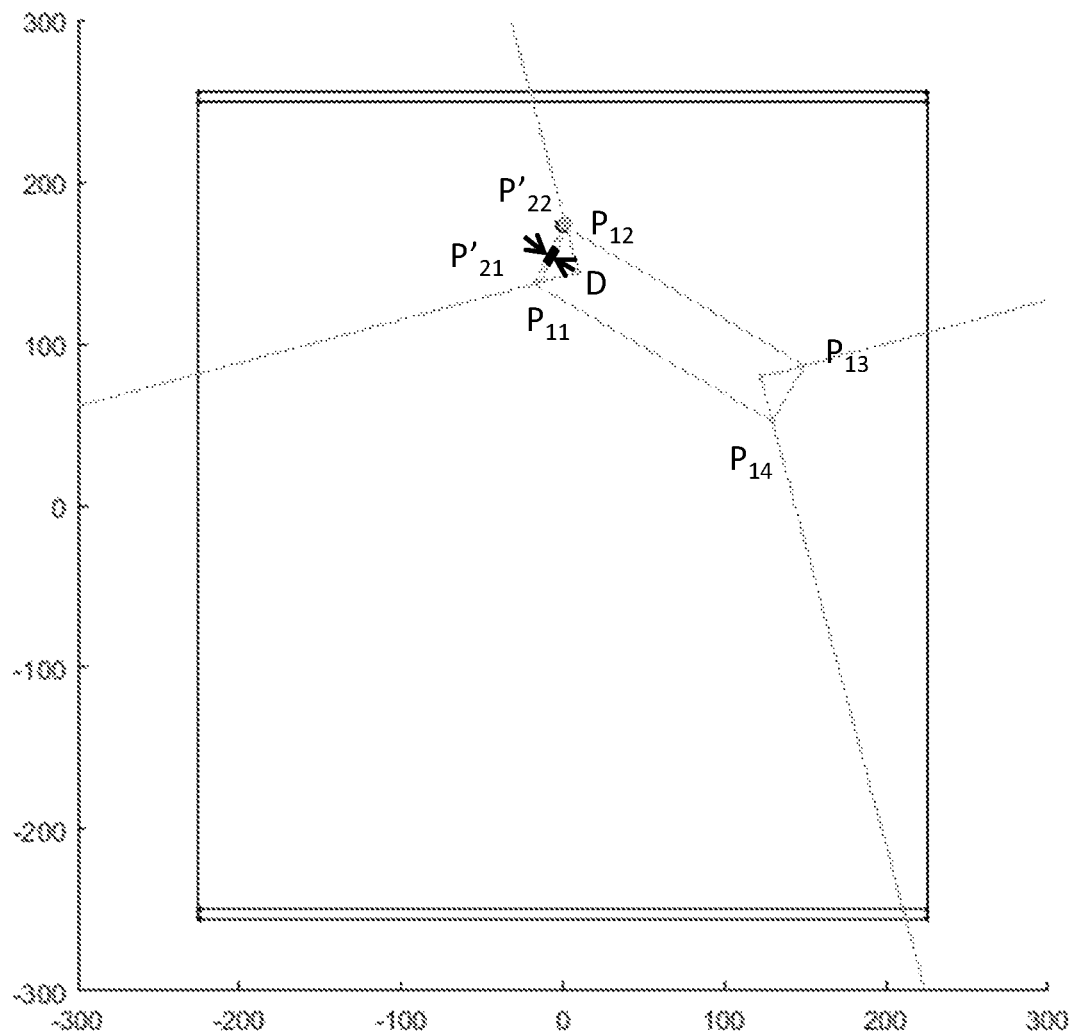

As shown in FIG. 8, distances between the linear portion connecting temporary vertices P'$_{21}$ and P'$_{22}$ and the linear portion between P$_{11}$ and P$_{12}$ are calculated. Since the linear portion connecting temporary vertices P'$_{21}$ and P'$_{22}$ and the linear portion between P$_{11}$ and P$_{12}$ may not be parallel, there are multiple distances between the two linear portions. At block 309, a determination is made as to whether the smallest distance D among the multiple distances between the two linear portions is less than or equal to TCCM. If it is determined at block 309 that the smallest distance D among the multiple distances is less than or equal to TCCM, then at block 311 the temporary distance D$_{p2to5}$ is increased by a predetermined amount and the above procedures of blocks 302 through 309 are repeated, including by using the equations (9)-(13) until the smallest distance D is greater than TCCM. The final result of VVM is set as the value for the vertex-to-vertex minimum.

Figure 11:
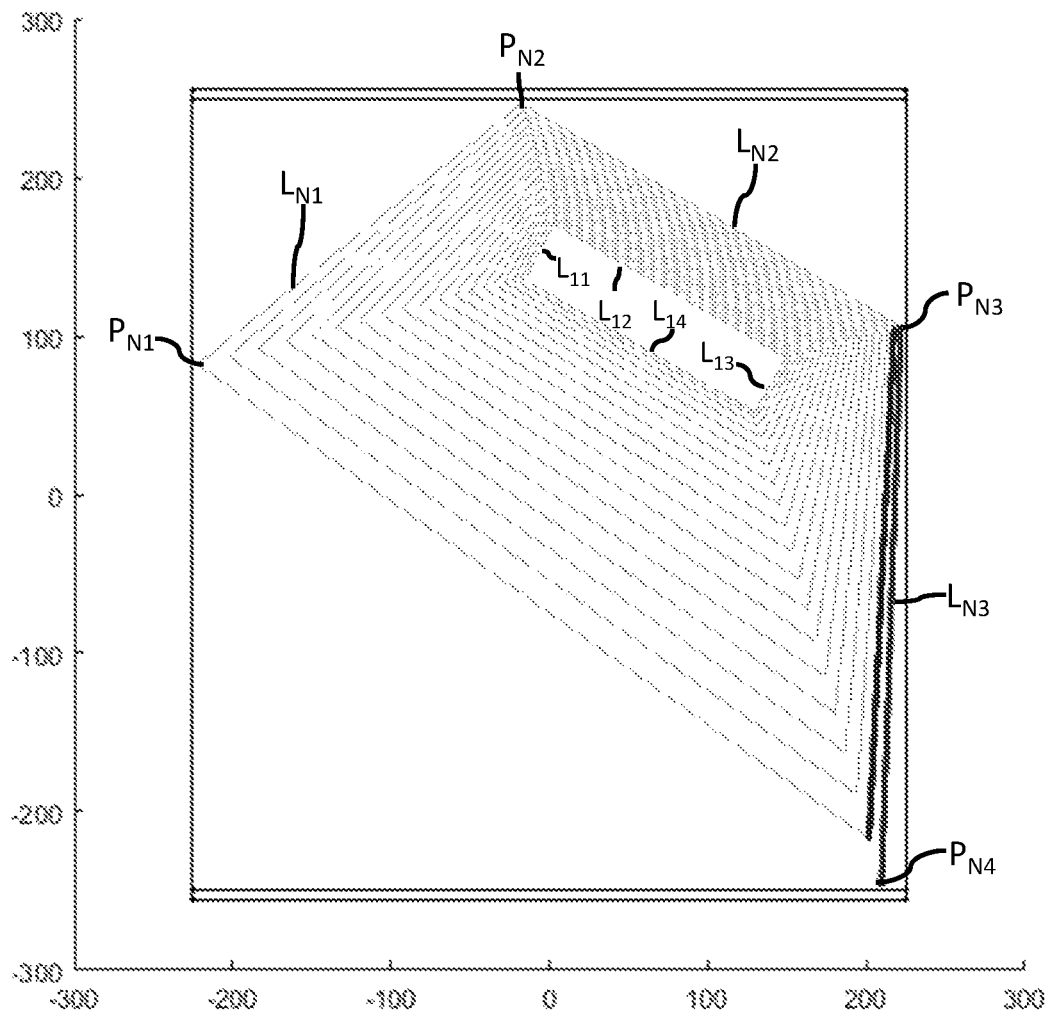

If, on the other hand, it is determined at block 309 that the smallest distance D among the multiple distances is greater than TCCM, then at block 312 a planar antenna layout is generated by interconnecting the planar antenna vertices by way of respective straight linear portions to form multiple loops (e.g., N loops) that sequentially traverse each of the plurality of diagonal lines of the respective planar antenna. Each of the loops includes multiple straight linear portions and multiple planar antenna vertices, namely four straight linear portions and four planar antenna vertices, in a case where the seed shape is a seed rectangle. For example, the first loop of each loop antenna, such as the loop antenna shown in FIG. 11, includes four vertices (i.e., P$_{11}$, P$_{12}$, P$_{13}$, and P$_{14}$) and four linear portions (i.e., L$_{11}$ connecting between P$_{11}$ and P$_{12}$, L$_{12}$ connecting P$_{12}$ and P$_{13}$, L$_{13}$ connecting P$_{13}$ and P$_{14}$, and L$_{14}$ connecting P$_{14}$ and P$_{21}$); . . . the (N–1)-th loop includes four vertices (i.e., P$_{(N-1)1}$, P$_{(N-1)2}$, P$_{(N-1)3}$, and P$_{(N-1)4}$) and four linear portions (i.e., L$_{(N-1)1}$ connecting between P$_{(N-1)1}$ and P$_{(N-1)2}$, L$_{(N-1)2}$ connecting P$_{(N-1)2}$ and P$_{(N-1)3}$, L$_{(N-1)3}$ connecting P$_{(N-1)3}$ and P$_{(N-1)4}$, and L$_{(N-1)4}$ connecting P$_{(N-1)4}$ and P$_{N1}$) (for clarity, not labeled in FIG. 11); and the N-th loop includes four vertices (i.e., P$_{N1}$, P$_{N2}$, P$_{N3}$, and P$_{N4}$) and three linear portions (i.e., L$_{N1}$ connecting P$_{N1}$ and P$_{N2}$, L$_{N2}$ connecting P$_{N2}$ and P$_{N3}$, and L$_{N3}$ connecting P$_{N3}$ and P$_{N4}$). FIG. 11 shows a design for a loop antenna that includes a plurality of loops, which is designed according to the procedure 300.

At block 313, multiple additional straight linear portions are routed from at least two of the planar antenna vertices (in particular, from the two terminal antenna vertices located at the two ends, respectively, of the linear planar antenna layout) to one or more connector locations with respect to the coordinate system of the substrate. The multiple additional straight linear portions are added to the planar antenna layout. In embodiments where the procedure 300 is employed to design an antenna assembly that includes multiple planar antennas to be arranged on respective layers of a multiple-layer substrate, the planar antenna layouts may be routed to a single connector location, or to separate connector locations corresponding to each antenna, respectively, or to any combination of connectors.

Figure 12:
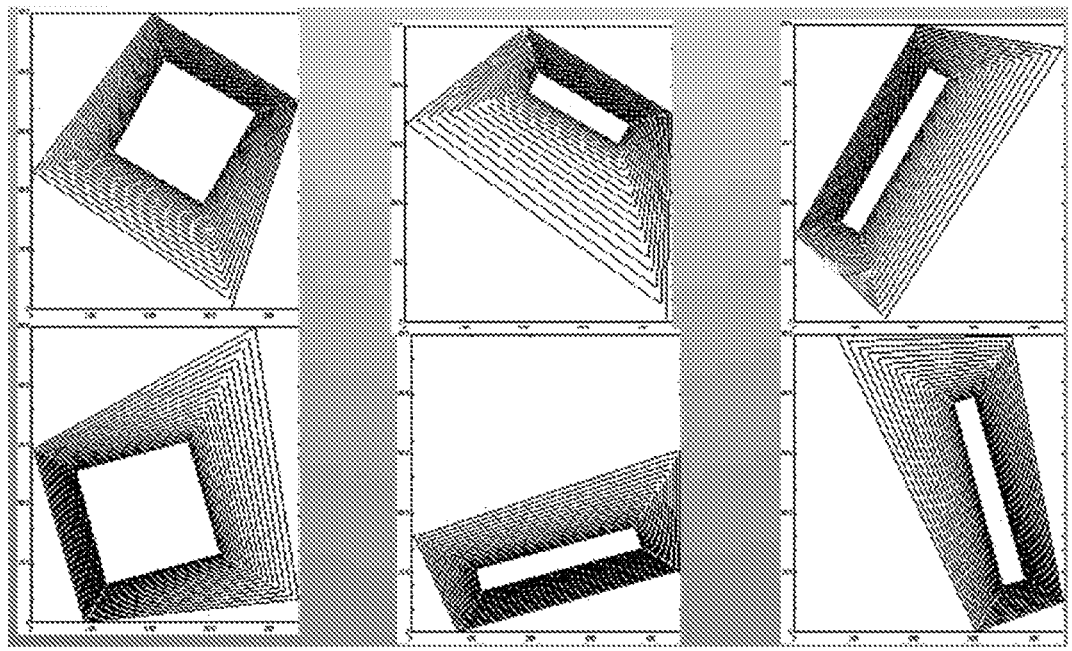
FIG. 12 is an illustration of multiple example antennas that may be designed according to the procedure of FIG. 3, in accordance with an embodiment of the present disclosure.

At block 314, the antenna index i$_{antenna}$ is compared to the number of antennas M of the antenna assembly to determine whether the procedures of block 302 through block 313 are to be repeated for additional antennas of the antenna assembly. If it is determined at block 314 that i$_{antenna}$ is less than the number of antennas M, then at block 315 i$_{antenna}$ is incremented by one to correspond to the next antenna (for example, the second antenna) of the M antennas of the antenna assembly. Then the procedures of block 302 through block 313 are repeated for that next antenna in the manner described above. FIG. 12 shows designs for six loop antennas, which can be designed in accordance with the procedure 300.

If, on the other hand, it is determined at block 314 that i$_{antenna}$ is equal to the number of antennas M, indicating that the procedures of block 302 through block 313 have been executed for each of the M antennas of the antenna assembly, then at block 316, which may be optional in some embodiments, data corresponding to the generated planar antenna layout is exported to a circuit board routing tool, a circuit board manufacturing tool, and/or an electromagnetic simulation tool.

In one example, by exporting the data corresponding to the generated planar antenna layout to the electromagnetic simulation tool at block 316, one or more electromagnetic fields that may be generated by the antennas of the antenna assembly may be simulated based on the exported data and on the superposition of multiple electromagnetic field components from each of the multiple straight linear portions of the planar antenna layout, respectively. For instance, each loop based on the seed shape can be expressed with a definite mathematical equation, such as a Cartesian equation or a parametric equation, such that the strength of an EM field generated by each loop can be calculated by the Biot-Savart-Laplace law at any point in space based on the mathematical equation. In other words, by virtue of geometrical and other aspects of the antenna assembly (such as the use of straight linear portions as the interconnections in the antennas of the antenna assembly), the need to generate and employ a detailed electromagnetic field mapping can be avoided by instead enabling an electromagnetic field mapping to be theoretically computed based on the characteristics of the antenna assembly. The computed electromagnetic field mapping can then be employed either alone or in conjunction with a more easily generated low-density electromagnetic field mapping obtained from measurements. In other words, the antenna assembly designed according to the procedure 300 can serve as the basis upon which to generate an accurate high-density theoretical electromagnetic field mapping for EMN, without having to use expensive measuring equipment and without having to perform time-consuming and laborious measurements.

As is apparent from the description herein, according to the procedure 300, an antenna assembly can be efficiently and designed in a repeatable manner based on a few design parameters and/or constraints, such as a seed shape, a number of loops, a TCCM, and/or the like. Each of the antennas of the designed antenna assembly can be printed, deposited, or fabricated on a respective substrate layer and can be used as the EM field generator 145 of the EMN system 100 of FIG. 1. Further, by virtue of employing straight linear portions to constitute the loop antennas, electromagnetic fields generated by each linear portion can be theoretically and accurately calculated using the Biot-Savart-Laplace law at any point in the EM volume.

Figure 13:
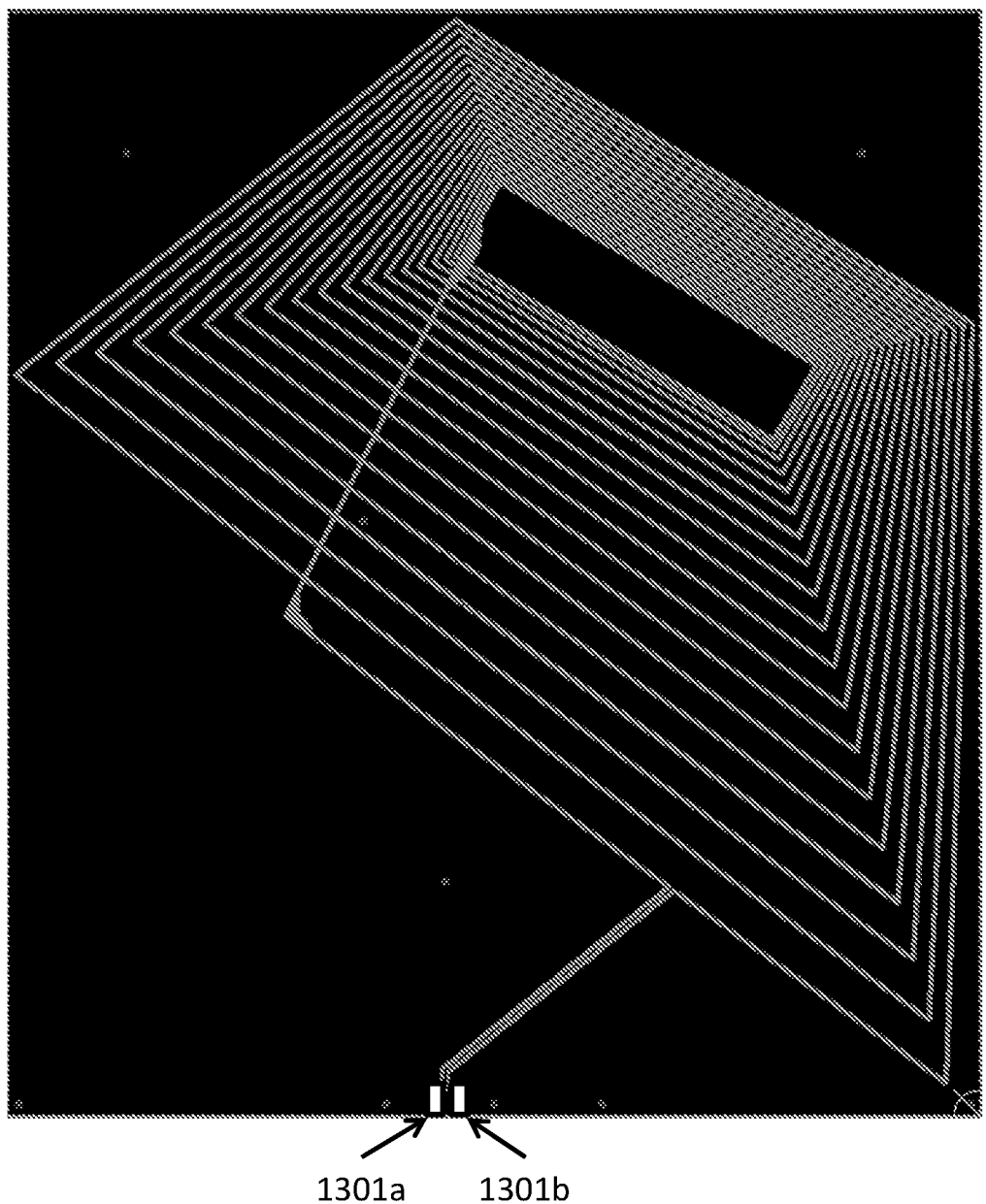
FIG. 13 shows an example design of a loop antenna layout trace placement, in accordance with an embodiment of the present disclosure.

FIG. 13 shows a graphical illustration of a loop antenna layout designed by the method 300 of FIG. 3. After connecting all the vertices, additional layout may be automatically generated based on a few design rules in place related to trace length and routing directionality. These rules may be specific to a PCB software program or design requirements. In an aspect, the antenna design made by the method 300 may be converted to a 2 dimensional DXF (Drawing eXchange Format) CAD file, which is then imported into Altium PCB layout software. PCB layout software is not limited to Altium PCB layout software but can be any software, which a person having ordinary skill in the art would readily appreciate and use.

Based on the design rules or design requirements of the software, vertices $P_{11}$ and $P_{N4}$ are electrically coupled to a connector 1301, which includes at least two conductors 1301a, 1301b of the loop antenna, respectively, and a full blueprint of the loop antenna is complete.

Upon completion of the design of the antenna assembly, an antenna is fabricated, based on the antenna assembly design, by depositing electrically conducting materials (e.g., silver or copper) on a substrate, as shown in FIG. 13. The antenna printed on the substrate includes structural and/or geometrical relationships between loops, which are described in detail below.

In an example aspect, vertices of the loop antenna can be grouped in four groups. The first group of vertices includes $P_{11}, P_{21}, \ldots,$ and $P_{N1}$, the second group of vertices includes $P_{12}, P_{22}, \ldots,$ and $P_{N2}$, the third group of vertices includes $P_{13}, P_{23}, \ldots,$ and $P_{N3}$, and the fourth group of vertices includes $P_{14}, P_{24}, \ldots,$ and $P_{N4}$. Because $V_{layout\_k}$ is different for each group, one group of vertices may be more densely distributed than the other groups of vertices. As shown in FIG. 13, vertices in the fourth group are more loosely distributed than vertices in the other groups, and the vertices in the second or third group are more densely distributed than vertices in the first and fourth groups.

In another aspect, the shortest distance between two corresponding linear portions (e.g., $L_{jk}$ and $L_{(j+1)k}$) increases as j increases. In other words, the distances between two adjacent corresponding linear portions are increasing in a direction from the innermost linear portion to the corresponding outermost linear portion. Based on this structural and/or geometrical relationship among loops and vertices, the loop antenna can cover the substrate as much as possible while maintaining such a relationship.

In an embodiment, after connecting the vertices with linear portions, another safety measure may be employed to confirm that all the requirements are satisfied in the antenna design. For example, shortest distances between two adjacent corresponding linear portions may be calculated again. In a case when there are any two adjacent corresponding linear portions, between which the shortest distance is not greater than TCCM, the procedure 300 can be repeated with a different minimum vertex to vertex distance VVM.

In an aspect, the design procedure 300 can enable maintaining substantially the same inductance of each loop antenna because the inductance is defined based at least in part on the antenna geometry. The resistance of the loop antenna may vary with copper thickness on each layer. Thus, in order to ensure that the antenna assembly maintains the intended copper thickness, two additional layers (one on the top and the other on the bottom) are added. With these extra layers, the plating processing for the vias would not add copper to the antenna layers on the internal layers. Thus, the copper thickness may depend only on the core material used and copper weight selected, initially. In another aspect, the PCB design may contain more than a single via for each current carrying path to minimize series resistance and increase the robustness of each current path. By having more vias, the resistance can be predicted and automatically calculated with high accuracy based on the antenna geometry and controlled copper thickness.

Figure 14:
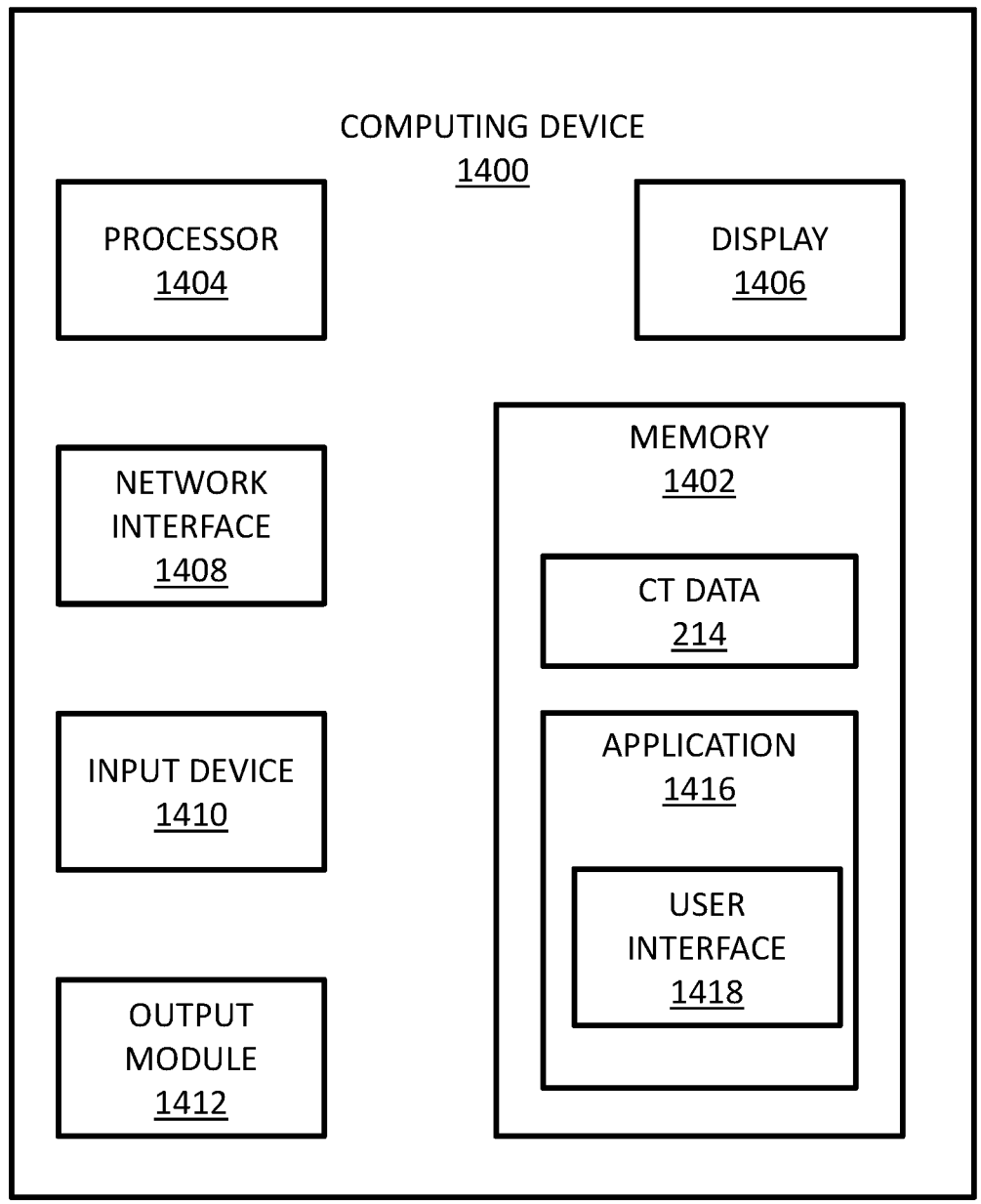
FIG. 14 is a block diagram of an example computing device for use in various embodiments of the present disclosure.
Figure 15A:
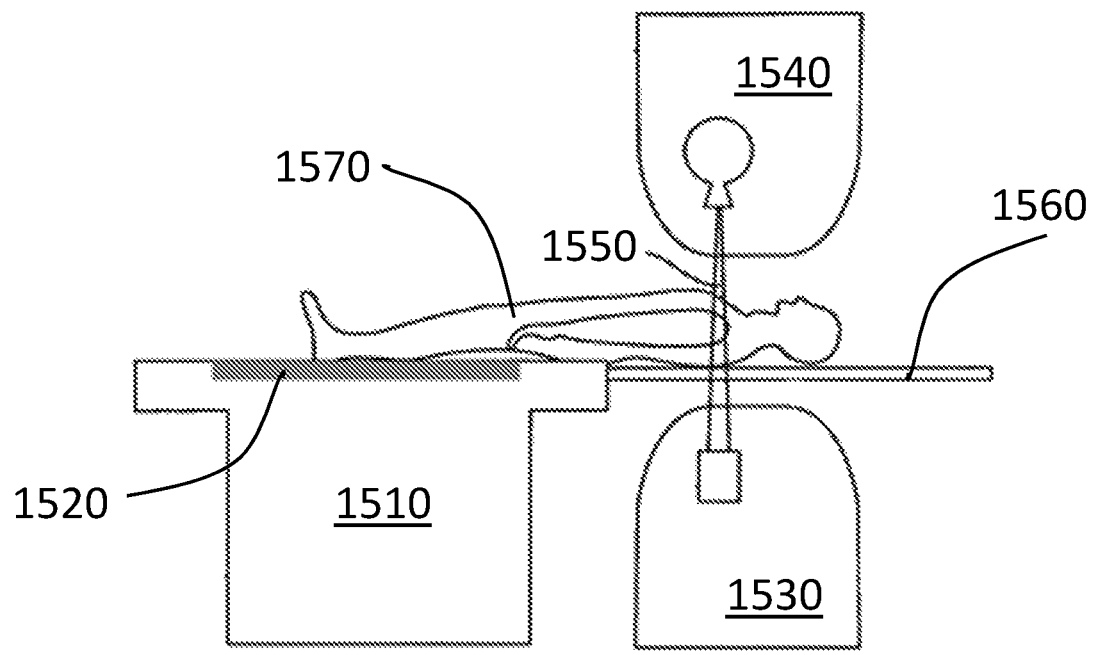
FIGS. 15A and 15B are schematic illustrations of a patient table and CT scanner in combination with an EMN system in different positions in accordance with an embodiment of the present disclosure.
Figure 15B:
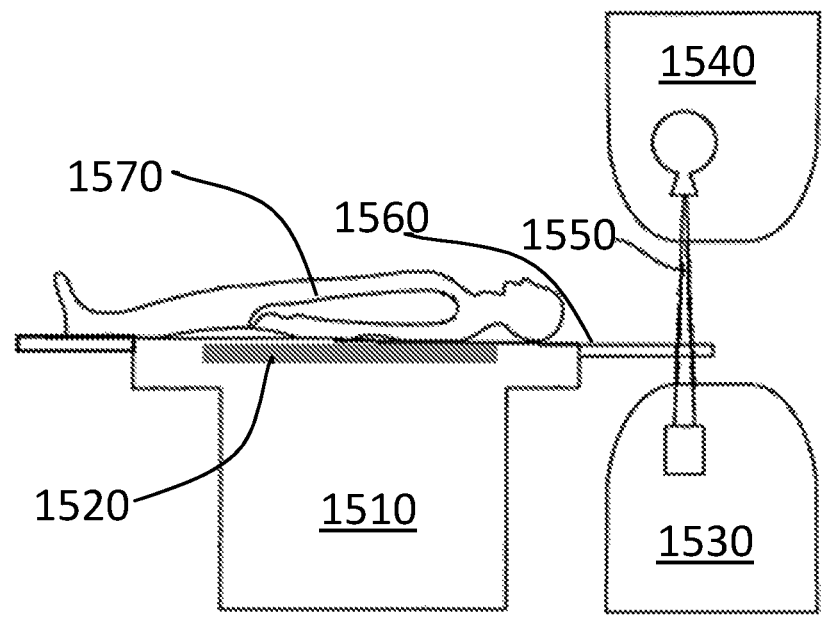

Turning now to FIG. 14, there is shown a block diagram of a computing device 1400, which can be used as the EMN system 100, the control workstation 102, the tracking device 160, a computer performing the procedure 300 of FIG. 3, and/or a controller for gantry table 1560 of FIGS. 15A and 15B. The computing device 1400 may include one or more of each of the following components: a memory 1402, a processor 1404, a display 1406, network interface controller 1408, an input device 1410, and/or an output module 1412.

The memory 1402 includes any non-transitory computer-readable storage media for storing data and/or software that is executable by the processor 1404 and which controls the operation of the computing device 1400. In an embodiment, the memory 1402 may include one or more solid-state storage devices such as flash memory chips. Alternatively, or in addition to the one or more solid-state storage devices, the memory 1402 may include one or more mass storage devices connected to the processor 1404 through a mass storage controller (not shown in FIG. 14) and a communications bus (not shown in FIG. 14). Although the description of computer-readable media contained herein refers to a solid-state storage, it should be appreciated by those skilled in the art that computer-readable storage media can be any available media that can be accessed by the processor 1404. That is, examples of computer readable storage media include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 1400.

The memory 1402 may store application 1416 and/or data 1414. The application 1416 may, when executed by the processor 1404, cause the display 1406 to present user interface 1418 on the display 1406.

The processor 1404 may be a general purpose processor, a specialized graphic processing unit (GPU) configured to perform specific graphics processing tasks while freeing up the general purpose processor to perform other tasks, a programmable logic device such as a field programmable gate array (FPGA) or complex programmable logic device (CPLD), and/or any number or combination of such processors or devices configured to work independently or cooperatively.

The display 1406 may be touch-sensitive and/or voice-activated, enabling the display 1406 to serve as both an input and output device. Alternatively, a keyboard (not shown), mouse (not shown), or other data input devices may be employed.

The network interface 1408 may be configured to connect to a network, such as a local area network (LAN) including a wired network and/or a wireless network, a wide area network (WAN), a wireless mobile network, a Bluetooth network, and/or the Internet. For example, the computing device 1400 may receive design requirements and predetermined variables and perform the procedure 300 of FIG. 3 to design an antenna assembly. The computing device 1400 may receive updates to its software, for example, application 1416, via the network interface controller 1408. The computing device 1400 may also display notifications on the display 1406 that a software update is available.

In another aspect, the computing device 1400 may receive computed tomographic (CT) image data of a patient from a server, for example, a hospital server, Internet server, or other similar servers, for use during surgical planning. Patient CT image data may also be provided to the computing device 1400 via a removable memory (not shown in FIG. 14).

Input device 1410 may be any device by means of which a user may interact with the computing device 1400, such as, for example, a mouse, keyboard, foot pedal, touch screen, and/or voice interface.

Output module 1412 may include any connectivity port or bus, such as, for example, parallel ports, serial ports, universal serial busses (USB), or any other similar connectivity port known to those skilled in the art.

The application 1416 may be one or more software programs stored in the memory 1402 and executed by the processor 1404 of the computing device 1400. During a design phase for loop antennas, one or more software programs in the application 1416 may be loaded from the memory 1402 and executed by the processor 1404 to automatically design loop antennas, given certain parameters and/or constraints, such as seed shape information, the number of loops in each loop antenna, and/or the like. In some embodiments, during a planning phase, one or more programs in the application 1416 guides a clinician through a series of steps to identify a target, size the target, size a treatment zone, and/or determine an access route to the target for later use during the navigation or procedure phase. In some other embodiments, one or more software programs in the application 1416 may be loaded on computing devices in an operating room or other facility where surgical procedures are performed, and is used as a plan or map to guide a clinician performing a surgical procedure, but without any feedback from the medical device used in the procedure to indicate where the medical device is located in relation to the plan.

The application 1416 may be installed directly on the computing device 1400, or may be installed on another computer, for example a central server, and opened on the computing device 1400 via the network interface 1408. Application 1416 may run natively on the computing device 1400, as a web-based application, or any other format known to those skilled in the art. In some embodiments, the application 1416 will be a single software program having all of the features and functionality described in the present disclosure. In other embodiments, the application 1416 may be two or more distinct software programs providing various parts of these features and functionality. For example, the application 1416 may include one software program for automatically designing loop antennas, another one for converting the design into a CAD file, and a third program for PCB layout software program. In such instances, the various software programs forming part of the application 1416 may be enabled to communicate with each other and/or import and export various data including settings and parameters relating to the design of the loop antennas. For example, a design of a loop antenna generated by one software program may be stored and exported to be used by a second software program to convert into a CAD file, and the converted file may be also stored and exported to be used by a PCB layout software program to complete a blueprint of the loop antenna.

The application 1416 may communicate with a user interface 1418 which generates a user interface for presenting visual interactive features to a user, for example, on the display 1406 and for receiving input, for example, via a user input device. For example, user interface 1418 may generate a graphical user interface (GUI) and output the GUI to the display 1406 for viewing by a user.

In a case that the computing device 1400 may be used as the EMN system 100, the control workstation 102, or the tracking device 160, the computing device 1400 may be linked to the monitoring device 130, thus enabling the computing device 1400 to control the output on the monitoring device 130 along with the output on the display 1406. The computing device 1400 may control the monitoring device 130 to display output which is the same as or similar to the output displayed on the display 1406. For example, the output on the display 1406 may be mirrored on the monitoring device 130. Alternatively, the computing device 1400 may control the monitoring device 130 to display different output from that displayed on the display 1406. For example, the monitoring device 130 may be controlled to display guidance images and information during the surgical procedure, while the display 1406 is controlled to display other output, such as configuration or status information of an electrosurgical generator (not shown in FIG. 1).

The application 1416 may include one software program for use during the planning phase, and a second software program for use during the navigation or procedural phase. In such instances, the various software programs forming part of application 1416 may be enabled to communicate with each other and/or import and export various settings and parameters relating to the navigation and treatment and/or the patient to share information. For example, a treatment plan and any of its components generated by one software program during the planning phase may be stored and exported to be used by a second software program during the procedure phase.

FIGS. 15A and 15B are schematic illustrations of gantry table 1560, upper CT scanner component 1540, and lower CT scanner component 1530, in combination with EMN system 1520 in different positions in accordance with an embodiment of the present disclosure. Upper CT scanner component 1540 and lower CT scanner component 1530 form in combination a CT scanner that scans along CT scan plane 1550. A CT scanner may be useful during a surgical procedure. EMN system 1520 may also be useful during a surgical procedure, but it causes interference with, and/or is interfered with by, the CT scanner. Therefore, EMN system 1520 is housed in patient table housing 1510, which is also equipped with gantry table 1560. Gantry table 1560 is operable to move patient 1570 between upper CT scanner component 1540 and lower CT scanner component 1530 so that patient 1570 is bisected by CT scan plane 1550, as shown in FIG. 15A. Gantry table 1560 is further operable to move patient 1570 away from upper CT scanner component 1540 and lower CT scanner component 1530, and onto EMN system 1520 so that patient 1570 may be scanned by EMN system 1520, as shown in FIG. 15B.

Figure 16A:
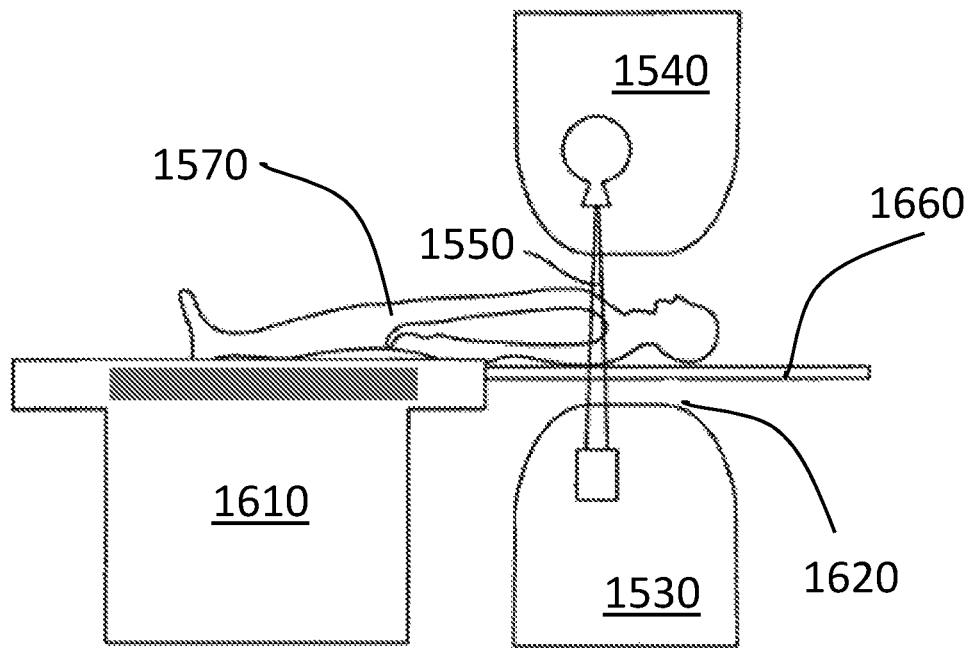
FIGS. 16A and 16B are schematic illustrations of another patient table and CT scanner in combination with an EMN system in different positions in accordance with another embodiment of the present disclosure.
Figure 16B:
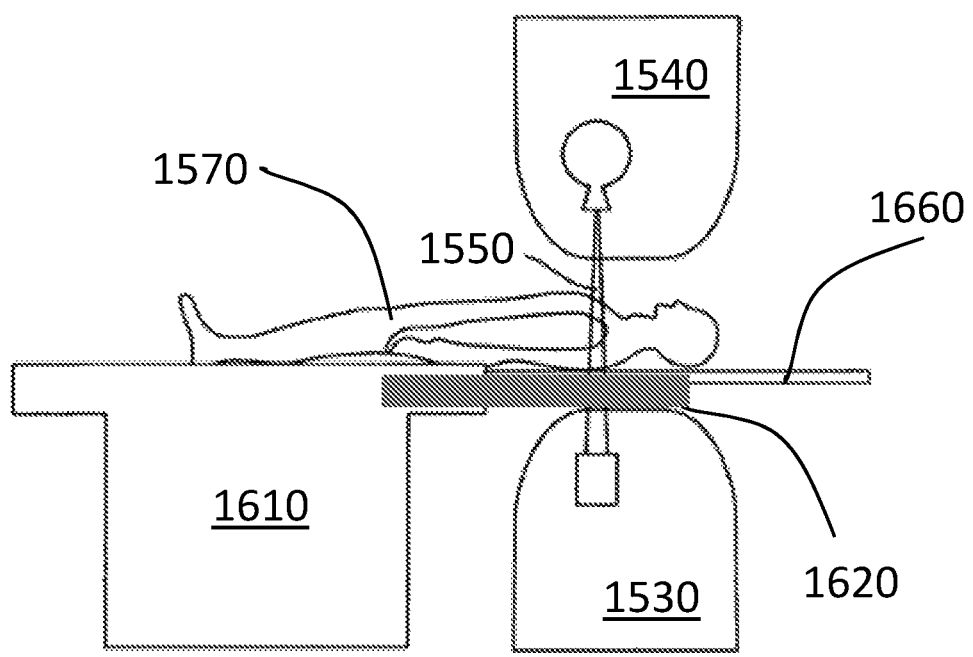

FIGS. 16A and 16B are schematic illustrations of gantry table 1660, upper CT scanner component 1540, and lower CT scanner component 1530, in combination with EMN system 1620 in different positions in accordance with an embodiment of the present disclosure. In this alternative arrangement, EMN system 1620 is moved beneath the surface of, or with, gantry table 1660, and may be in CT scan plane 1550 when the CT scanner is not in use, and moved away from CT scan plane 1550 when the CT scanner is being used. In this embodiment, patient table housing 1610 may move with EMN system 1620 and/or gantry table 1660, or alternatively may be stationary with one or both of EMN system 1620 and gantry table 1660 moving relative to patient table housing 1610. In still further embodiments, both the CT scanner and EMN system 1520 may be mobile, and may optionally move in tandem while the patient remains substantially motionless.

Although embodiments have been described in detail with reference to the accompanying drawings for the purpose of illustration and description, it is to be understood that the inventive processes and apparatus are not to be construed as limited. It will be apparent to those of ordinary skill in the art that various modifications to the foregoing embodiments may be made without departing from the scope of the disclosure.

Detailed embodiments of such devices, systems incorporating such devices, and methods using the same are described above. However, these detailed embodiments are merely examples of the disclosure, which may be embodied in various forms. Therefore, specific structural and functional details disclosed herein are not to be interpreted as limiting but merely as a basis for the claims and as a representative basis for allowing one skilled in the art to variously employ the present disclosure in virtually any appropriately detailed structure. While the example embodiments described above are directed to the bronchoscopy of a patient's airways, those skilled in the art will realize that the same or similar devices, systems, and methods may also be used in other lumen networks, such as, for example, the vascular, lymphatic, and/or gastrointestinal networks. Those skilled in the art would also recognize that the same or similar devices, systems, and methods may also be used to perform a percutaneous procedure or in procedures in which a device is navigated through a luminal network before puncturing through a wall in the luminal network to reach a target.

Though written generally as applying to bronchoscopic and percutaneous approaches for treatment and diagnostic procedures, those of skill in the art will readily recognize that these same or similar techniques, systems and methods may be employed for laparoscopic approaches (e.g., using one or more transdermal ports and a laparoscopic camera) or other endoscopic approaches when accessing other portions of the body including but not limited to the large and small intestine, the vascular networks, cardiac spaces, and the like. In an aspect, the procedural space for the envisioned system is open, percutaneous or laparoscopic liver and kidney ablation.

What is claimed is:

1. A system including a patient table and a computed tomography (CT) scanner, the system comprising:
   a patient table housing supporting a gantry table mounted on top of the patient table housing, wherein the gantry table is movable relative to the patient table housing to move a patient toward and away from a computed tomography (CT) scan plane defined by an upper CT scanner component and a lower CT scanner component;
   an electromagnetic navigation (EMN) system disposed within the patient table housing, the EMN system including an antenna assembly having a plurality of planar loop antennas each configured for radiating at least one electromagnetic field for electromagnetic navigation, wherein the EMN system and the upper and lower CT scanner components are movable together in tandem relative to the gantry table and the EMN system is movable relative to the gantry table independently from the upper and lower CT scanner components; and
   a moving arrangement including an electromagnet coupled to the EMN system and configured to be controlled via a user interface to:
   move the EMN system relative to the gantry table and the upper and lower CT scanner components; and
   move the EMN system away from the upper and lower CT scanner components while the upper and lower CT scanner components are activated to generate the CT scan plane and the gantry table maintains the patient within the CT scan plane.

2. The system according to claim 1, wherein the moving arrangement is configured to move the gantry table in a direction perpendicular to the CT scan plane.

3. The system according to claim 1, wherein the user interface includes one of a hand held remote control, a cable tethered switch, or a button on a graphical user interface electrically coupled to a processor.

4. The system according to claim 1, wherein the moving arrangement includes at least one of a rail structure or a plurality of wheels.

5. The system according to claim 1, wherein at least a portion of the gantry table includes CT compatible materials.

6. The system according to claim 1, wherein the gantry table is configured to move between a first position and a second position, the patient in the first position being located above the EMN system to enable tracking of surgical tools, the patient in the second position being located in the CT scan plane.

7. The system according to claim 1, wherein a distance between any two adjacent planar loop antennas of the antenna assembly progressively increases in a direction from an innermost planar loop antenna to an outermost planar loop antenna.

\* \* \* \* \*